(12) United States Patent
Taylor et al.

(10) Patent No.: US 10,278,819 B2
(45) Date of Patent: May 7, 2019

(54) CARDIAC VALVE REPAIR DEVICES CONFIGURED FOR PERCUTANEOUS DELIVERY

(71) Applicant: Edwards Lifesciences Corporation, Irvine, CA (US)

(72) Inventors: David M. Taylor, Lake Forest, CA (US); Tri D. Tran, Fountain Valley, CA (US); Sean Chow, Tustin, CA (US); David L. Hauser, Newport Beach, CA (US); Pui Tong Ho, Ladera Ranch, CA (US); Alexander H. Cooper, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 137 days.

(21) Appl. No.: 15/167,760

(22) Filed: May 27, 2016

(65) Prior Publication Data

US 2016/0346084 A1    Dec. 1, 2016

Related U.S. Application Data

(60) Provisional application No. 62/169,395, filed on Jun. 1, 2015.

(51) Int. Cl.
*A61F 2/24* (2006.01)

(52) U.S. Cl.
CPC .......... *A61F 2/2445* (2013.01); *A61F 2/243* (2013.01); *A61F 2/2418* (2013.01);
(Continued)

(58) Field of Classification Search
CPC ...... A61F 2210/0014; A61F 2002/8486; A61F 2/2445; A61F 2/2466; A61F 2/243;
(Continued)

(56) References Cited

U.S. PATENT DOCUMENTS 5,824,066 A    10/1998    Gross
5,968,053 A    10/1999    Revelas
(Continued)

FOREIGN PATENT DOCUMENTS

CA    246991 A1    3/2003
WO    90/09153 A1    8/1990
(Continued)

OTHER PUBLICATIONS

International Search Report for PCT/US2016/034602 dated Sep. 9, 2016.

*Primary Examiner* — Eric J Rosen
*Assistant Examiner* — Chima U Igboko
(74) *Attorney, Agent, or Firm* — Jie Lian; Klarquist Sparkman, LLP

(57) ABSTRACT

Disclosed herein are devices for improving coaption of the mitral valve leaflets to reduce or eliminate mitral valve regurgitation. The devices may be used to perform mitral valve annuloplasty, or to serve as a docking station for a transcatheter prosthetic heart valve. The various embodiments of devices are configured for percutaneous and, in some cases, transvascular delivery. Delivery systems useful for routing the devices to the mitral valve are also disclosed, including catheters, balloons and/or mechanical expansion systems. The devices themselves include at least one tissue penetrating member. Methods of delivery include partially embedding the devices in the mitral valve annulus via at least one tissue penetrating member. Tissue penetrating members may be embedded into the tissue in a simultaneous or a nearly simultaneous fashion. Upon embedding, the devices employ various expansion and/or contraction features to adjust the mitral valve diameter. Adjustments may continue until the leaflets fully coapt and the problem of mitral regurgitation is reduced or eliminated.

24 Claims, 32 Drawing Sheets

(52) U.S. Cl.
CPC .......... *A61F 2/2433* (2013.01); *A61F 2/2466* (2013.01); *A61F 2/2448* (2013.01); *A61F 2210/0014* (2013.01); *A61F 2250/0014* (2013.01)

(58) Field of Classification Search
CPC ........ A61F 2/2433; A61F 2/2418; A61F 2/82; A61F 2/848; A61F 2/86; A61F 2/88; A61F 2/885; A61F 2/89; A61F 2/90; A61F 2/91; A61F 2/915; A61F 2/92; A61F 2/94; A61F 2/2409; A61F 2/2442; A61F 2/2469; A61F 2/2427; A61F 2/2412; A61F 2002/8483; A61F 2002/91508; A61F 2002/91516; A61F 2002/91525; A61F 2002/91533; A61F 2002/9155; A61F 2220/0008; A61F 2220/0075; A61F 2220/0016; A61F 2250/006; A61F 2250/0063; A61F 2250/007; A61F 2250/0073; A61F 2250/0069

See application file for complete search history.

(56) References Cited

U.S. PATENT DOCUMENTS

| | | | |
|---|---|---|---|
| 5,984,959 A | 11/1999 | Robertson et al. | |
| 6,001,127 A | 12/1999 | Schoon et al. | |
| 6,210,432 B1 | 4/2001 | Solem et al. | |
| 6,355,030 B1 | 3/2002 | Aldrich et al. | |
| 6,582,460 B1 | 6/2003 | Cryer | |
| 6,702,826 B2 | 3/2004 | Liddicoat et al. | |
| 6,726,716 B2 | 4/2004 | Marquez | |
| 6,776,791 B1 | 8/2004 | Stallings et al. | |
| 6,790,231 B2 | 9/2004 | Liddicoat et al. | |
| 6,913,608 B2 | 7/2005 | Liddicoat et al. | |
| 6,942,694 B2 | 9/2005 | Liddicoat et al. | |
| 7,007,698 B2 | 3/2006 | Thornton | |
| 7,063,722 B2 | 6/2006 | Marquez | |
| 7,081,131 B2 | 7/2006 | Thornton | |
| 7,482,936 B2 | 1/2009 | Bolling | |
| 7,556,647 B2 | 7/2009 | Drews et al. | |
| 7,591,848 B2 | 9/2009 | Allen | |
| 8,226,707 B2 | 7/2012 | White | |
| 8,551,161 B2 | 10/2013 | Dolan | |
| 9,192,471 B2 | 11/2015 | Bolling | |
| 2002/0188344 A1* | 12/2002 | Bolea | A61F 2/90 623/1.11 |
| 2004/0019374 A1* | 1/2004 | Hojeibane | A61F 2/2412 623/1.13 |
| 2005/0182290 A1 | 8/2005 | Lau et al. | |
| 2006/0025855 A1 | 2/2006 | Lashinski et al. | |
| 2006/0106456 A9 | 5/2006 | Machold et al. | |
| 2006/0178732 A1* | 8/2006 | Chobotov | A61F 2/07 623/1.34 |
| 2006/0178733 A1 | 8/2006 | Pinchuk et al. | |
| 2006/0184240 A1 | 8/2006 | Jimenez et al. | |
| 2006/0184241 A1 | 8/2006 | Marquez | |
| 2006/0235509 A1* | 10/2006 | Lafontaine | A61F 2/2418 623/2.11 |
| 2006/0282147 A1* | 12/2006 | Andreas | A61F 2/91 623/1.11 |
| 2007/0005129 A1 | 1/2007 | Damm et al. | |
| 2007/0016287 A1 | 1/2007 | Cartledge et al. | |
| 2007/0027533 A1 | 2/2007 | Douk | |
| 2007/0239272 A1 | 10/2007 | Navia et al. | |
| 2008/0027483 A1 | 1/2008 | Cartledge et al. | |
| 2008/0167713 A1 | 7/2008 | Bolling | |
| 2008/0228266 A1 | 9/2008 | McNamara et al. | |
| 2008/0262609 A1 | 10/2008 | Gross et al. | |
| 2009/0149872 A1 | 6/2009 | Gross et al. | |
| 2009/0287299 A1 | 11/2009 | Tabor et al. | |
| 2010/0121433 A1 | 5/2010 | Bolling et al. | |
| 2010/0249920 A1 | 9/2010 | Bolling et al. | |
| 2011/0218620 A1* | 9/2011 | Meiri | A61B 17/0487 623/2.11 |
| 2011/0224785 A1 | 9/2011 | Hacohen | |
| 2012/0053680 A1 | 3/2012 | Bolling et al. | |
| 2013/0218266 A1* | 8/2013 | Chalekian | A61F 2/2433 623/2.11 |
| 2013/0268044 A1* | 10/2013 | Parsons | A61F 2/07 623/1.2 |

FOREIGN PATENT DOCUMENTS

| | | |
|---|---|---|
| WO | 93/15690 A2 | 8/1993 |
| WO | 97/12565 A1 | 4/1997 |
| WO | 97/20524 A1 | 6/1997 |
| WO | 98/24386 A1 | 6/1998 |
| WO | 99/29269 A1 | 6/1999 |
| WO | 99/49816 A1 | 10/1999 |
| WO | 00/44311 A2 | 8/2000 |
| WO | 00/62715 A1 | 10/2000 |
| WO | 01/89440 A2 | 11/2001 |
| WO | 03/017 874 A1 | 3/2003 |
| WO | 03/080150 A2 | 10/2003 |
| WO | 03/105670 A2 | 12/2003 |
| WO | 03/105730 A1 | 12/2003 |
| WO | 04/014282 A2 | 2/2004 |
| WO | 04/030569 A2 | 4/2004 |
| WO | 04/032717 A2 | 4/2004 |
| WO | 04/103223 A1 | 12/2004 |
| WO | 05/002424 A2 | 1/2005 |
| WO | 05/007037 A1 | 1/2005 |
| WO | 05/046488 A2 | 5/2005 |
| WO | 06/086434 A1 | 8/2006 |
| WO | 07/021834 A1 | 2/2007 |
| WO | 08/088716 A1 | 7/2008 |

\* cited by examiner

CARDIAC VALVE REPAIR DEVICES CONFIGURED FOR PERCUTANEOUS DELIVERY

CROSS REFERENCE TO RELATED APPLICATION

This application claims the benefit of U.S. Provisional Patent Application No. 62/169,395, filed Jun. 1, 2015, which is incorporated herein by reference.

BACKGROUND

The native heart valves (i.e., the aortic, pulmonary, tricuspid and mitral valves) serve critical functions in assuring the forward flow of an adequate supply of blood ugh the cardiovascular system. These heart valves can be rendered less effective by congenital malformations, inflammatory processes, infectious conditions or disease.

Mitral valve regurgitation occurs when the posterior and anterior leaflets fail to fully close during systole. This enables blood to leak backward into the left atrium during contraction. The most common cause of mitral regurgitation is age-related connective tissue degeneration. Degenerative valve diseases occur at an annual incidence rate of 2-3% in industrialized nations. Mitral regurgitation may also be caused by cardiac ischemia, cardiac dilation/remodeling, Rheumatic fever, Marfan's syndrome, and other diseases and disorders.

Such damage to the valves can result in serious cardiovascular compromise or death. For many years the definitive treatment for such disorders was the surgical repair or replacement of the valve during open heart surgery. However, such surgeries are highly invasive and are prone to many complications. Therefore, elderly or frail patients with defective heart valves often go untreated.

Minimally invasive, transvascular techniques now enable surgeons to access cardiac valves without open-heart surgery. Catheters are inserted into vasculature at a site that is relatively distant from the heart. The catheters carry therapeutic devices through the patient's vasculature and to the malfunctioning heart valve. Once there, the devices are deployed within the valve to prevent further backflow of blood. For example, a transvascular technique has been developed for introducing and implanting a prosthetic heart valve using a flexible catheter in a manner that is much less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (e.g., bottom tip) of the heart. Transapical techniques are disclosed in U.S. Patent Application Publication No. 2007/0112422. Like the transvascular approach, the transapical approach can include a balloon catheter having a steering mechanism for delivering a balloon-expandable prosthetic heart valve through an introducer to the aortic annulus. The balloon catheter can include a deflecting segment just proximal to the distal balloon to facilitate positioning of the prosthetic heart valve in the proper orientation within the aortic annulus.

The above techniques and others have provided numerous options for high operative risk patients with aortic valve disease to avoid the consequences of open heart surgery and cardiopulmonary bypass. While devices and procedures for the aortic valve are well developed, such catheter-based procedures are not necessarily applicable to the mitral valve due to the distinct differences between the aortic and mitral valve. The mitral valve has a complex subvalvular apparatus, i.e., chordae tendinae, which are not present in the aortic valve.

Surgical mitral valve repair techniques (e.g., mitral annuloplasty) have increased in popularity due to their high success rates and clinical improvements noted after repair. In addition to the existing mitral valve repair technologies, there are a number of new technologies aimed at making mitral valve repair a less invasive procedure. These technologies range from iterations of the Alfieri stitch procedure to coronary sinus-based modifications of mitral anatomy to subvalvular applications or ventricular remodeling devices, which would incidentally correct mitral regurgitation.

However, for mitral valve replacement, few less-invasive options are available. There are approximately 25,000 mitral valve replacements (MVR) each year in the United States. However, it is estimated that over 300,000 patients who meet guidelines for treatment are denied treatment based on their age and/or co-morbidities. Thus, a need exists for minimally invasive techniques for replacing the mitral valve.

SUMMARY

Disclosed herein are implementations of mitral valve repair devices. The devices may be used to perform mitral valve annuloplasty, or to serve as a docking station for a transcatheter prosthetic heart valve. The various embodiments of devices are configured for percutaneous and, in some cases, transvascular delivery. Delivery systems useful for routing the devices to the mitral valve are also disclosed, including catheters, balloons and/or mechanical expansion systems. The devices themselves include at least one tissue penetrating member. Methods of delivery include partially embedding the devices in the mitral valve annulus via at least one tissue penetrating member. Tissue penetrating members may be embedded into the tissue in a simultaneous or nearly simultaneous fashion. Upon embedding, the devices employ various expansion and/or contraction features to adjust the mitral valve diameter. Adjustments may continue until the leaflets fully coapt and the problem of mitral regurgitation is reduced or eliminated.

Mitral valve regurgitation is used herein as an example of a valvular disorder that may be addressed using the disclosed devices and methods. However, the disclosed devices and methods could be adapted for use with the aortic valve, the pulmonic valve and/or the tricuspid valve.

Disclosed herein are devices for improving the function of a cardiac valve. The devices may be used to perform mitral valve annuloplasty, or to serve as a docking station for a transcatheter prosthetic heart valve. The various embodiments of devices are configured for percutaneous and, in some cases, transvascular delivery. Delivery systems useful for routing the devices to the mitral valve are also disclosed, including catheters, balloons and/or mechanical expansion systems. The devices themselves may be circular in shape or non-circular in shape, and include at least one tissue penetrating member. Methods of delivery include partially embedding the devices in the mitral valve annulus via at least one tissue penetrating member. Tissue penetrating members are embedded into the tissue in a simultaneous or nearly simultaneous fashion. Upon embedding, the devices employ various expansion and/or contraction features to adjust the mitral valve diameter. Adjustments may continue until the leaflets fully coapt and the problem of mitral regurgitation is reduced or eliminated. In some implementations, the devices may be used as a docking station for a prosthetic mitral valve.

In some implementations, a device for improving function of a cardiac valve may include a frame configured to fit within a cardiac valve. The frame includes a proximal portion, a distal portion, and an opening extending therebetween. The frame is collapsible to a first position and expandable to a second position. In some implementations, the frame is at least partially formed from a shape memory material. In some implementations, shape memory and non-shape memory portions alternate along the perimeter of the frame.

The frame may include a pair of tissue penetrating members extending from the proximal portion of the frame. The tissue penetrating members have ends with tissue penetrating surfaces. In the first position, the tissue penetrating members are positioned such that the penetrating surfaces of each pair of tissue penetrating members abut one another to form a blunt end. In the second position, the penetrating members of each pair of tissue penetrating members are spaced apart such that their respective penetrating surfaces are exposed. In some implementations, the tissue penetrating members include tissue fixation mechanisms.

In some implementations, the frame may include a spiral tissue penetrating member. The method of percutaneous valve repair includes rotating the frame such that the spiral tissue penetrating member penetrates the tissue of the cardiac valve.

In some implementations, the frame includes a retrieval feature. For example, the retrieval feature may include a hole in the frame and a suture line running through the hole and connecting the frame to the catheter.

In some implementations, the frame is configured to retract from the second position and pull together the penetrated tissue.

In some implementations, a cinching device radially surrounds the frame and is used to adjust the overall diameter of the frame.

In some implementations, a device may include a frame with a lattice extending between the proximal and distal portions. The lattice includes a first plurality of struts and a second plurality of struts. Each strut of the second plurality is operably connected to at least one strut of the first plurality via respective connection points. The lattice also includes at least one expansion feature extending between at least two connection points. The expansion feature is configured to mechanically adjust positions of the connection points relative to one another. For example, the expansion feature may adjust the position of the connection points along an axis parallel to the longitudinal axis extending between proximal and distal portions of the frame. The expansion feature may include a tissue penetrating member.

Transcatheter delivery systems for the devices include a catheter for navigating the device through the cardiovascular system of a subject. In some implementations, delivery systems may include a plurality of rotation members configured to mechanically operate the expansion features of the device. In these implementations, a controller takes inputs from a user and operates the rotation members via a torque shaft. The rotation members couple to the expansion features and expand or contract the device based on inputs from the controller.

In some implementations, the transcatheter delivery systems includes a catheter, an elongate balloon, and a frame. The elongate balloon is configured to be attached to the catheter via an opening at the proximal end of the balloon. In the inflated state, the balloon has a proximal portion with a first diameter and a distal portion with a second diameter larger than the first diameter. The frame includes a proximal end, a distal end, and at least one tissue penetrating member extending from the frame. The frame surrounds at least a portion of the elongate balloon. When the elongate balloon is in the uninflated state, the frame is in a corresponding collapsed state. When the elongate balloon is in the inflated state, the frame is expanded to an expanded state. Methods of percutaneous valve repair includes navigating the uninflated elongate balloon and the collapsed frame through the cardiovascular system of a subject via the catheter, and positioning the elongate balloon and the frame within a cardiac valve of the subject. A gas or liquid is moved through the catheter and into the elongate balloon, causing the balloon to inflate and the frame to expand to the expanded state. A force may then be applied to the catheter in a manner that causes the at least one tissue penetrating member of the frame to penetrate the valvular tissue of the subject. The elongate balloon is then deflated such that the frame remains attached to the valvular tissue, and the catheter and elongate balloon are removed from the subject.

Some methods of percutaneous valve repair may include positioning the elongate balloon such that the proximal portion of the balloon is positioned between leaflets of the cardiac valve. In some implementations, the frame surrounds a portion of the proximal portion of the balloon. In other implementations, the frame surrounds a portion of the distal portion of the balloon. The elongate balloon may include a plurality of friction elements for increasing friction between the elongate balloon and the frame.

Further disclosed are methods for replacing a native mitral valve. The methods include advancing an expandable ring toward the mitral valve. The ring includes a collapsible and expandable frame. The frame includes a plurality of tissue penetrating members disposed along an exterior surface, and a plurality of protrusions along an inner surface. The ring is expanded such that the tissue penetrating members penetrate surrounding tissue within the mitral valve. The method further includes advancing a prosthetic valve toward the mitral valve. The prosthetic valve includes a collapsible and expandable tubular stent formed with intercrossing bars, as well as a valvular structure mounted within the tubular stent. The prosthetic valve is radially expanded within the ring, such that protrusions on the inner surface of the ring extend between intercrossing bars of the tubular stent. This secures the prosthetic valve to the ring, thereby anchoring the prosthetic valve within the native mitral valve.

In some implementations of the methods for replacing a native mitral valve, a delivery catheter is advanced toward the mitral valve. The delivery catheter includes a prosthetic valve disposed along its distal end portion. The prosthetic valve includes a collapsible and expandable tubular stent formed with intercrossing bars and a valvular structure mounted within the tubular stent. The method further includes radially expanding the prosthetic valve within the mitral valve and expanding a ring within the prosthetic valve. The ring includes a plurality of tissue penetrating members disposed along an exterior surface. The tissue penetrating members extend through the intercrossing bars of the tubular stent and penetrate surrounding tissue along the mitral valve, thereby securing the prosthetic valve to the native mitral valve.

DETAILED DESCRIPTION

The following description of certain examples of the medical apparatus should not be used to limit the scope of the medical apparatus. Other examples, features, aspects, embodiments, and advantages of the medical apparatus will become apparent to those skilled in the art from the following description, which is by way of illustration, one of the best modes contemplated for carrying out the medical apparatus. As will be realized, the medical apparatus is capable of other different and obvious aspects, all without departing from the spirit of the medical apparatus. For example, the devices and methods disclosed herein are described in the context of mitral valve repair. However, the devices and methods may also have use in other areas of the cardiac anatomy, for example, the aortic valve, the pulmonary valve, and/or the tricuspid valve. Accordingly, the drawings and descriptions should be regarded as illustrative in nature and not restrictive.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The Human Heart

Figure 1:
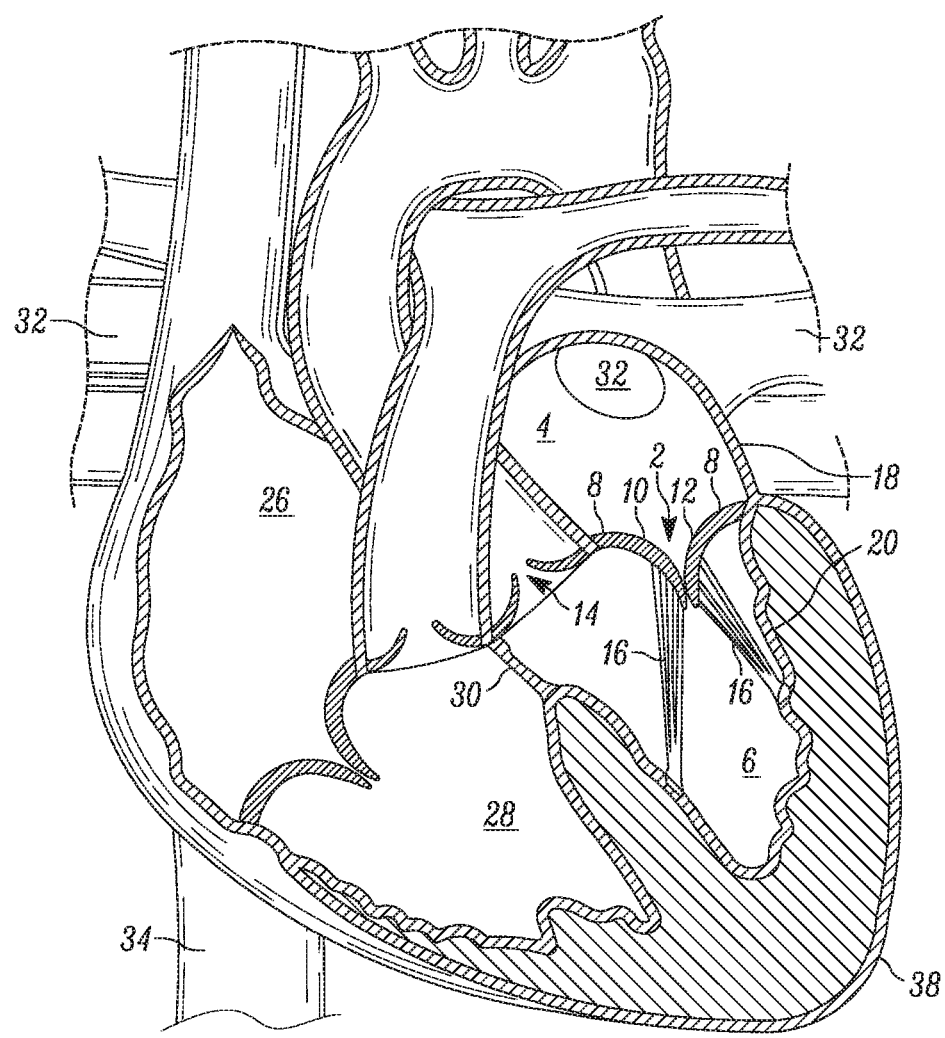
FIG. 1 is a cross section of a heart demonstrating the position of the native mitral valve. The mitral valve is in a closed position.
Figure 2:
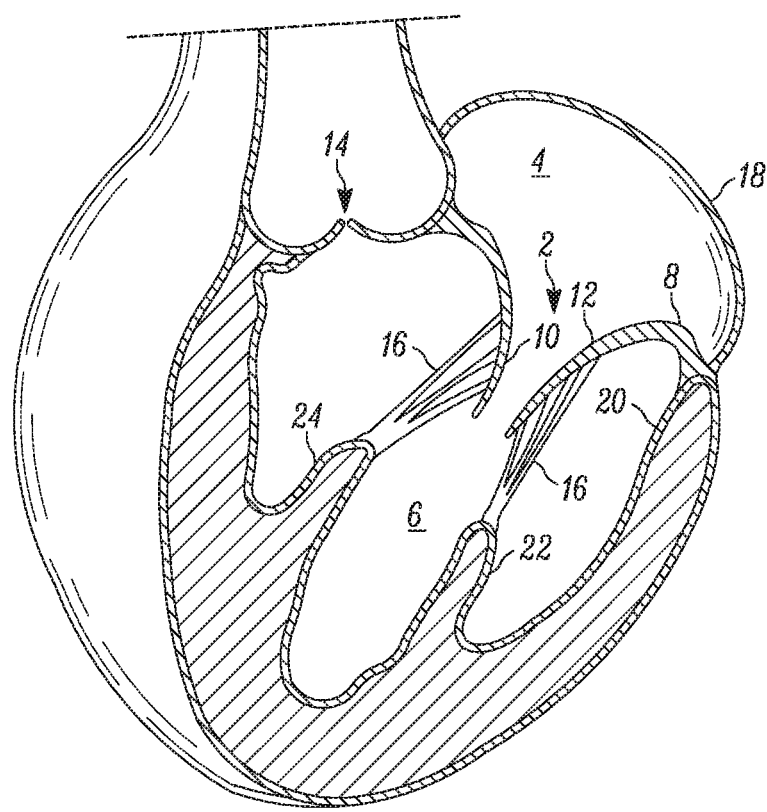
FIG. 2 is a cross section of a heart with the mitral valve in an open position.

Relevant portions of the human heart are shown in FIGS. 1 and 2. A healthy heart has a generally conical shape that tapers to a lower apex 38. The heart is four-chambered and comprises the left atrium 4, right atrium 26, left ventricle 6, and right ventricle 28. The left and right sides of the heart are separated by a wall generally referred to as the septum 30. The native mitral valve 2 of the human heart connects the left atrium 4 to the left ventricle 6. The mitral valve 2 has a very different anatomy than other native heart valves, such as the aortic valve 14.

The mitral valve 2 includes an annulus portion 8, which is an annular portion of the native valve tissue surrounding the mitral valve orifice, and a pair of cusps, or leaflets, 10, 12 extending downward from the annulus 8 into the left ventricle 6. The mitral valve annulus 8 can a "D" shaped, oval, or otherwise out-of-round cross-sectional shape having major and minor axes. The anterior leaflet 10 can be larger than the posterior leaflet 12, as shown schematically in FIGS. 3-4 forming a generally "C" shaped boundary between the abutting free edges of the leaflets when they are closed together.

Referring to FIG. 1, when operating properly, the anterior leaflet 10 and the posterior leaflet 12 function together as a one-way valve to allow blood to flow only from the left atrium 4 to the left ventricle 6. The left atrium 4 receives oxygenated blood from the pulmonary veins 32. When the muscles of the left atrium 4 contract and the left ventricle dilates, the oxygenated blood that is collected in the left atrium 4 flows into the left ventricle 6. When the muscles of the left atrium 4 relax and the muscles of the left ventricle 6 contract, the increased blood pressure in the left ventricle urges the two leaflets together, thereby closing the one-way mitral valve so that blood cannot flow back to the left atrium and is instead expelled out of the left ventricle through the aortic valve 14.

Figure 3:
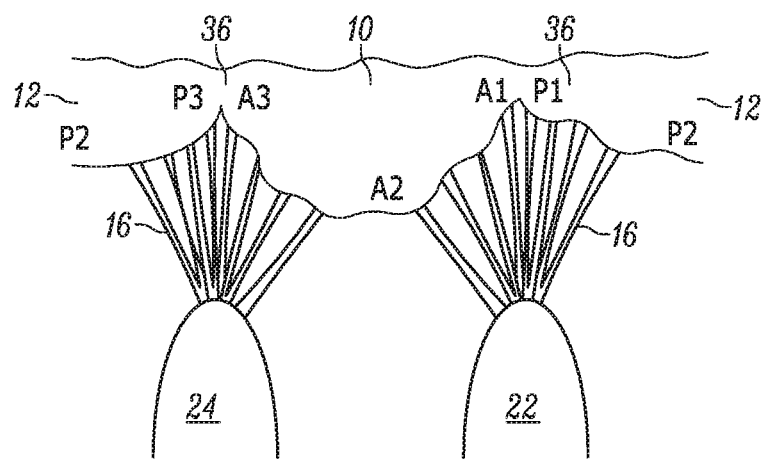
FIG. 3 is a schematic view of the native mitral valve anatomy showing the mitral leaflets attached to the papillary muscles via the chordae tendineae.
Figure 4:
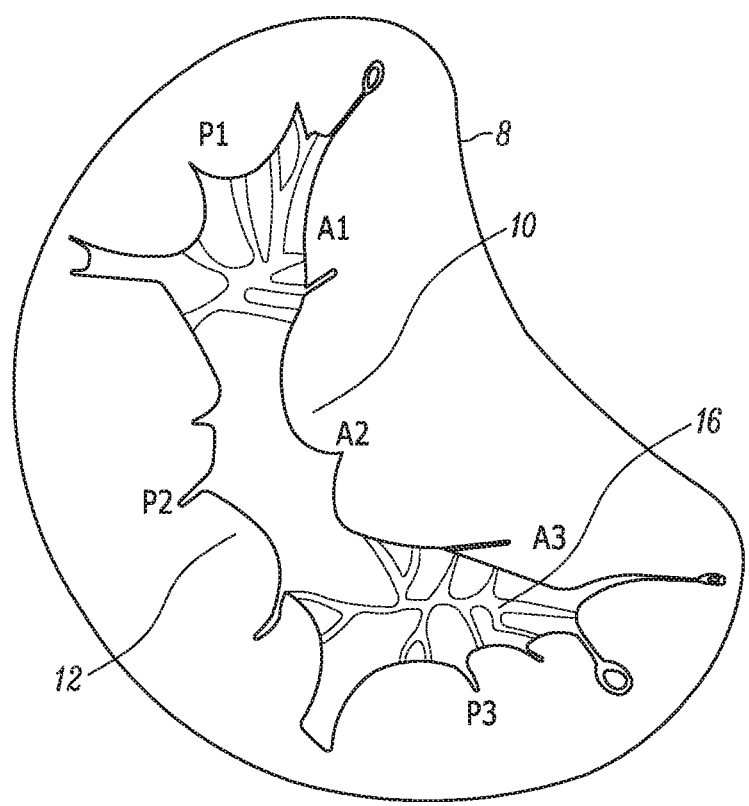
FIG. 4 depicts the native mitral valve as viewed from the left atrium.

To prevent the two leaflets 10, 12 from prolapsing under pressure and folding back through the mitral annulus 8 toward the left atrium 4, a plurality of fibrous cords called chordae tendinae 16 tether the leaflets 10, 12 to papillary muscles in the left ventricle 6. Referring to FIGS. 3 and 4, chordae 16 are attached to and extend between the postero-medial papillary muscle 22 and the postero-medial margins of both the anterior leaflet 10 and the posterior leaflet 12 (A1 and P1 areas, respectively, as identified by Carpentier nomenclature). Similarly, chordae 16 are attached to and extend between the antero-lateral papillary muscle 24 and the antero-lateral margins of both the anterior leaflet 10 and the posterior leaflet 12 (A3 and P3 areas, respectively, as identified by Carpentier nomenclature). Mitral valve regurgitation occurs when the anterior and posterior leaflets 10, 12 fail to fully close during systole. This enables blood to leak backward into the left atrium 4 during contraction.

Devices for Transvascular Mitral Valve Repair

Disclosed herein are devices for improving coaption of the mitral valve leaflets 10, 12 to reduce or eliminate mitral valve regurgitation. The devices may be used to perform mitral valve annuloplasty, or to serve as a docking station for a transcatheter prosthetic heart valve. The various embodiments of devices are configured for percutaneous and, in some cases, transvascular delivery. Delivery systems useful for routing the devices to the mitral valve are also disclosed, including catheters, balloons and/or mechanical expansion systems. The devices themselves include at least one tissue penetrating member. Methods of delivery include partially embedding the devices in the mitral valve annulus via at least one tissue penetrating member. Tissue penetrating members may be embedded into the tissue in a simultaneous or nearly simultaneous fashion. Upon embedding, the devices employ various expansion and/or contraction features to adjust the mitral valve diameter. Adjustments may continue until the leaflets fully coapt and the problem of mitral regurgitation is reduced or eliminated.

Figure 5A:
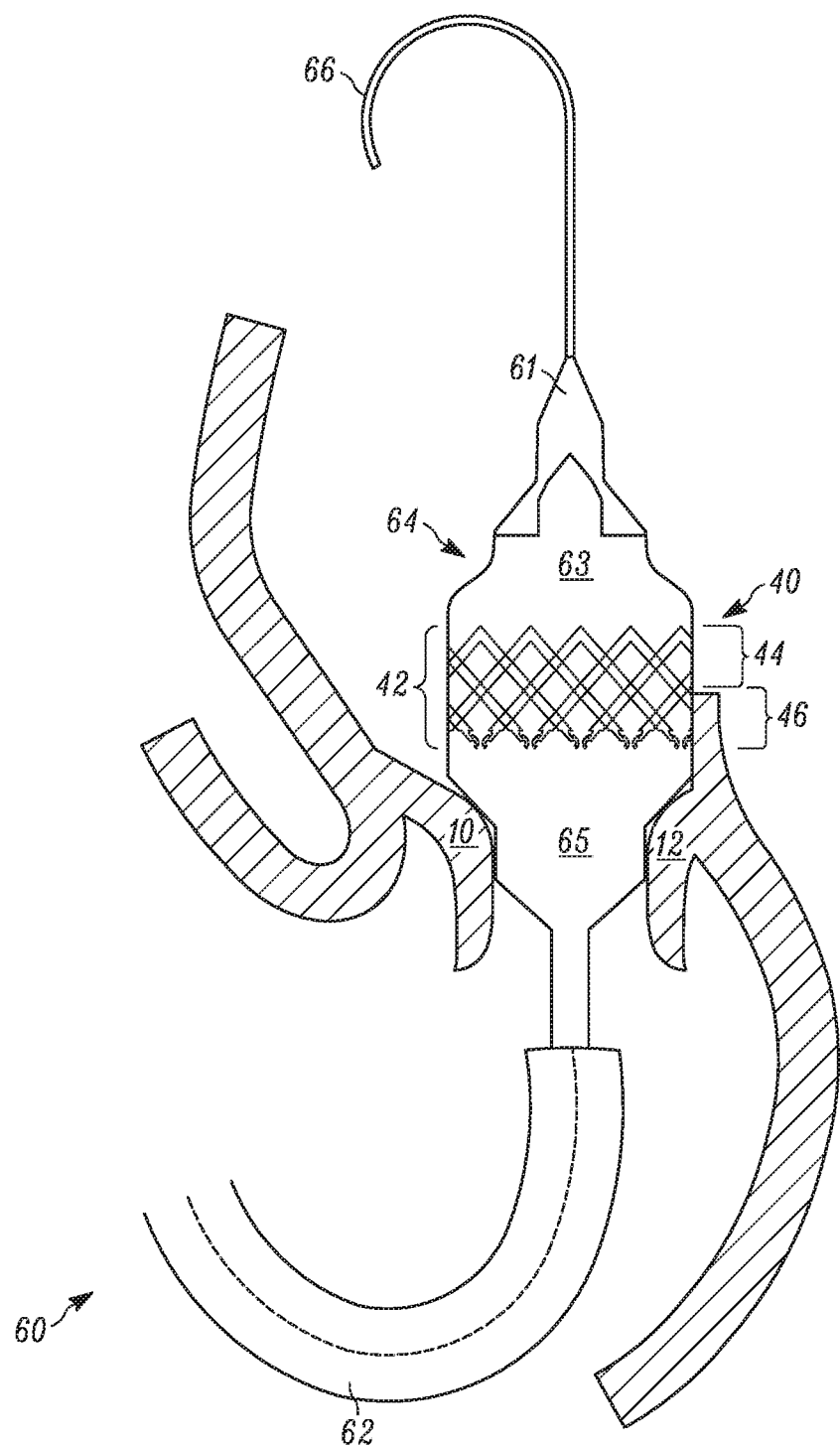
FIG. 5A is a side view of a device for mitral valve repair and a corresponding delivery system.

As an example of one embodiment, FIG. 5A shows a side view of a mitral valve undergoing treatment with an example mitral valve repair device 40 and device delivery system 60. Device 40 may be used to perform mitral valve annuloplasty, or to serve as a docking station for a transcatheter prosthetic heart valve. The frame 42 of the mitral valve repair device may have different implementations. In the embodiment of FIG. 5A, the mitral valve repair device has a frame 42 that is ring-like when viewed from above. In other implementations, the frame 42 may be shaped to suit the anatomy of the native mitral valve, or may create non-symmetrical constriction of the mitral valve annulus. For example, some implementations of the ring may be D-shaped when viewed from above. The sides of frame 42 may be latticed, as in FIG. 5A. Alternatively, the frame could be spiral shaped or solid as disclosed in later implementations. The frame is collapsible to facilitate delivery through the delivery catheter 62 of the delivery system 60. Once the device 40 is delivered to the proper surgical location, the balloon 64 is used to expand the frame.

Figure 5B:
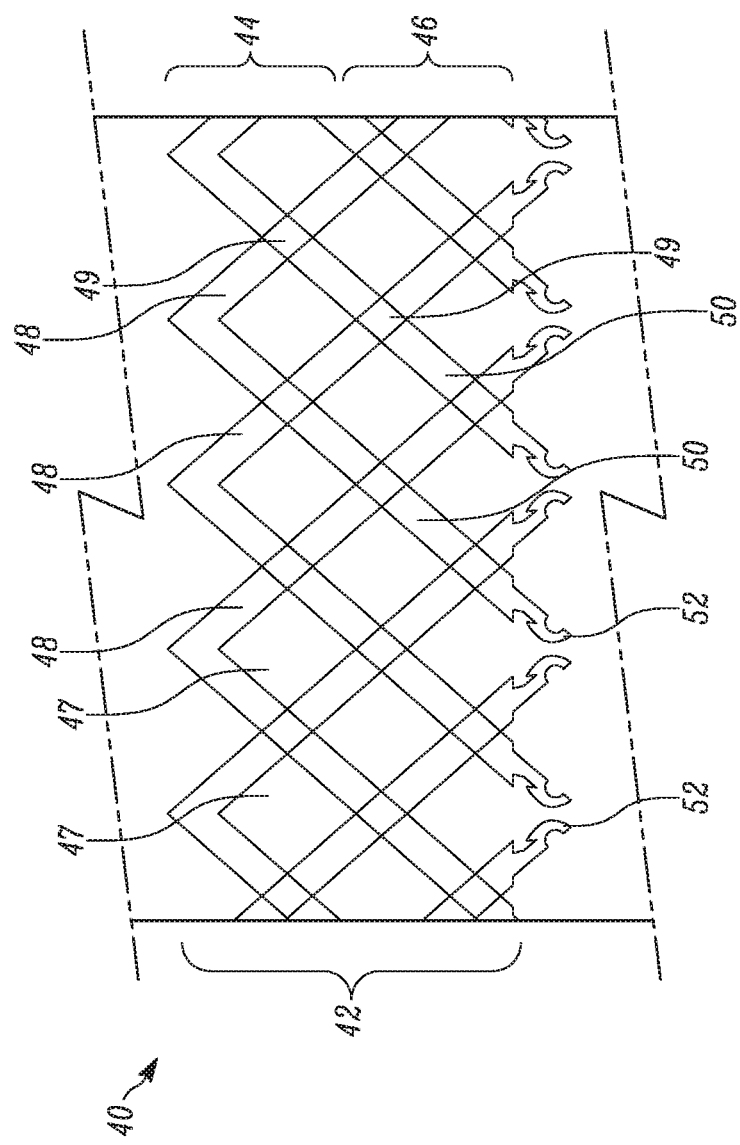
FIG. 5B is an enlarged view of the device shown in FIG. 5A.

The frame 42 shown in FIG. 5A includes a distal portion 44 terminating at a distal side and a proximal portion 46 terminating at a proximal side. During delivery, the distal portion 44 of the frame 42 is positioned farther from the delivery catheter 62 than the proximal portion. An enlarged illustration of the frame 42 of the embodiment shown in FIG. 5A is shown in FIG. 5B. The frame 42 includes a first series of parallel strut portions 48 extending between proximal and distal ends of the frame 42. The frame 42 also includes a second series of parallel strut portions 50. Each strut portion of the first series crosses at least one strut portion of the second series, meeting at a connection point 49. The frame 42 defines an opening extending between its distal and proximal portions 44, 46 in the direction of a central longitudinal axis. The struts also define a plurality of quadrangular spaces 47 positioned around the frame 42 in the circumferential direction. The frame 42 is collapsible to facilitate delivery through delivery catheter 62 and expandable to be deployed within the mitral valve using balloon 64.

As shown in FIG. 5B, tissue penetrating members 52 may extend from the proximal portion 46 of the frame. These serve to pierce the tissue and/or anchor the frame to the mitral valve annulus. The tissue penetrating members 52 include at least one penetrating point and/or sharp penetrating surface configured to cut through tissue. In some embodiments, the tissue penetrating members may also include tissue fixation mechanisms to prevent dislodgement of the device once the tissue has been cut and the tissue penetrating member is under the tissue. For example, tissue penetrating members may take the forms of hooks, barbs, anchors, screws, or coil-shaped anchors. In alternative embodiments, the tissue penetrating members 52 may flare outward from the frame 40 to better engage the tissue. In some cases, outwardly flaring tissue penetrating members 52 may be made of a shape memory material, such that the tissue penetrating members flare outwardly during expansion of the frame.

Figure 6A:
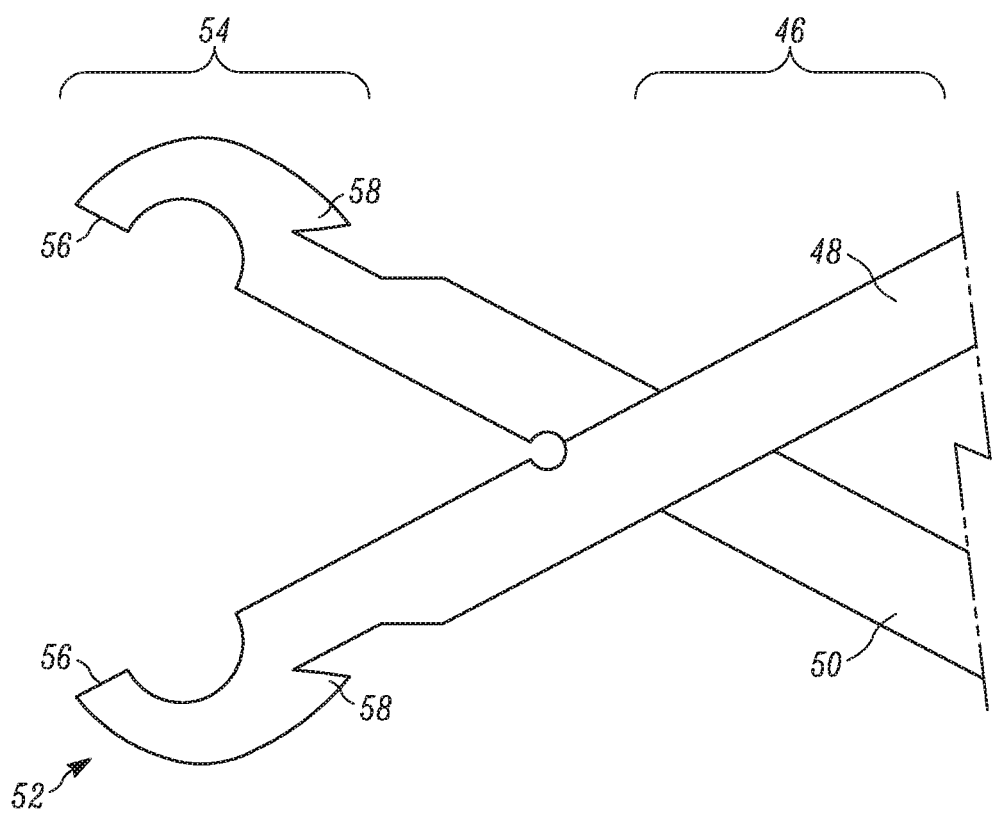
FIG. 6A is an enlarged view of the tissue penetrating members of the device shown in FIG. 5A. The tissue penetrating members are in an open position.
Figure 6B:
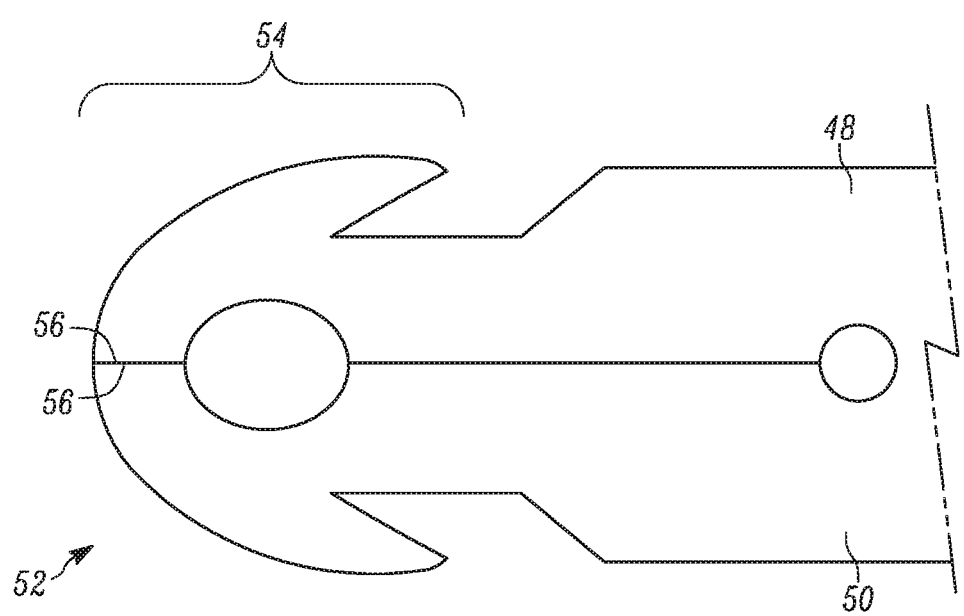
FIG. 6B is an enlarged view of the tissue penetrating members of the device shown in FIG. 5A. The tissue penetrating members are in a closed position.

The tissue penetrating members 52 extending from the proximal portion 46 of the frame shown in FIG. 5B are shown in expanded views in FIGS. 6A-B. Tissue penetrating members 52 include ends 54 with at least one penetrating surface 56. As shown in FIG. 6A, tissue penetrating members 52 may extend from the strut portions 48, 50 of the frame 42. When the struts of the frame are collapsed, these penetrating surfaces are brought together into an abutting relationship to blunt the end 54, as shown in FIG. 6B. This facilitates shielding of the penetrating surfaces 56 during the delivery of the device. Once the device reaches the valve and is expanded, the penetrating surfaces 56 are exposed as shown in FIG. 6A. In some embodiments, the tissue penetrating members are forced into the mitral valve tissue by a proximal movement of the balloon 64.

The tissue penetrating members shown in FIGS. 6A-B also include tissue fixation mechanisms in the form of barbs 58. For the implementation shown in FIG. 5B, the barbs 58 extend away from the tissue engagement member 52 at an angle and toward the frame 42. This prevents the tissue engagement members 52 from sliding backward within the tissue once embedded. A tissue engagement member 52 may have one tissue fixation mechanism, or it may have a plurality of tissue fixation mechanisms. Though FIGS. 5 and 6 show tissue fixation mechanisms in the form of barbs 58, they may take other forms, including but not limited to spines, hooks, bumps, ridges, or layers of porous materials.

The devices disclosed herein may be made using a polymer or a metal. For all embodiments described herein, some of the materials may be radio-opaque to assist in fluoroscopic monitoring. In some embodiments, portions of the mitral valve repair device may be formed of a shape memory material. Shape memory materials may include shape memory polymers or shape memory metals. For example, the shape memory materials may be nickel-titanium alloys. The shape memory materials may be shape set in a first position by, for example, heat conditioning. If the material is shape set by heat conditioning, it is then cooled. In the cooled state, it may be deformed to a second position. The second position is retained until a stimulus is applied, for example, heating above a critical temperature. The stimulus causes the shape memory material to revert back to its first position. While heat conditioning is given as an example process used to set a shape memory material, other types of conditioning may be performed to achieve the same purpose.

Figure 7A:
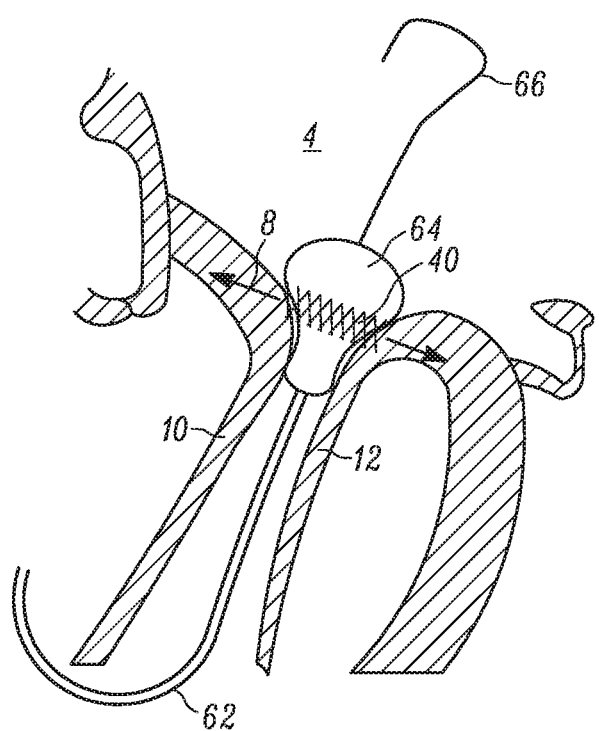
FIG. 7A is a side view of a device being expanded by a balloon within a native mitral valve. The device is made of a shape memory material.
Figure 7B:
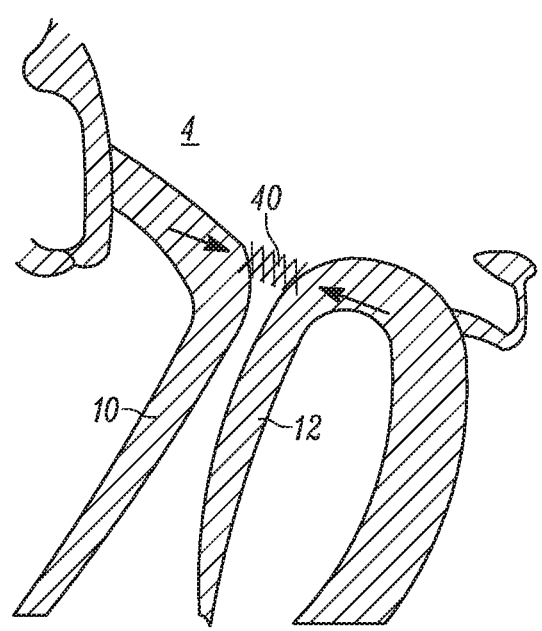
FIG. 7B is a side view of the device of FIG. 7A after removal of the balloon. The device retracts back to its shape set position.

For example, a mitral valve repair device 40 may be shape set in a first, collapsed position for moving through the patient's vascular system via delivery system 60. This provides a mechanism for securing the valve to the balloon during delivery. The balloon 64 may then expand the device 40 to a second position during deployment, as shown in FIG. 7A. As shown in FIG. 7B, the shape memory material contracts to its original, first position after the balloon 64 is removed because body temperature is above the critical temperature for the particular material. The frame thus exerts a continuous inward force, promoting coaption of the leaflets 10, 12 and reducing or eliminating mitral regurgitation.

A shape memory device 40 that promotes an inward constrictive force may not be optimal for all patients. For example, some disorders may cause the tissues of the mitral valve annulus 8 to weaken. In these cases, the tissue penetrating members 52 may be ripped out of the weakened annular tissue by the inwardly constrictive force. An alternative embodiment is a shape memory device 40 that is shape set in an expanded state. This device would open to its expanded state upon release from the delivery system 60, and would not contract after expansion. While it would not exert an inwardly constrictive force on the annulus, it could act against disease-related dilation of the annulus, slowing or preventing the progression of the disease.

Figure 8A:
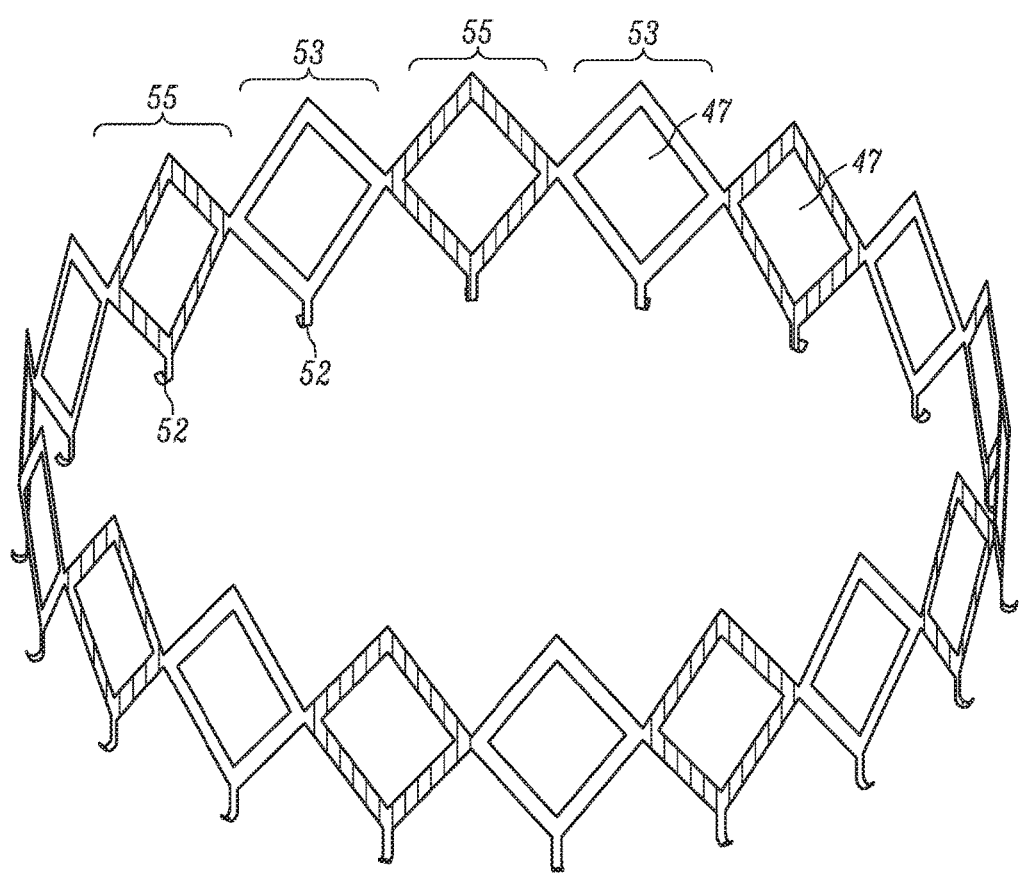
FIG. 8A depicts a device including alternating portions of shape memory and non-shape memory materials.
Figure 8B:
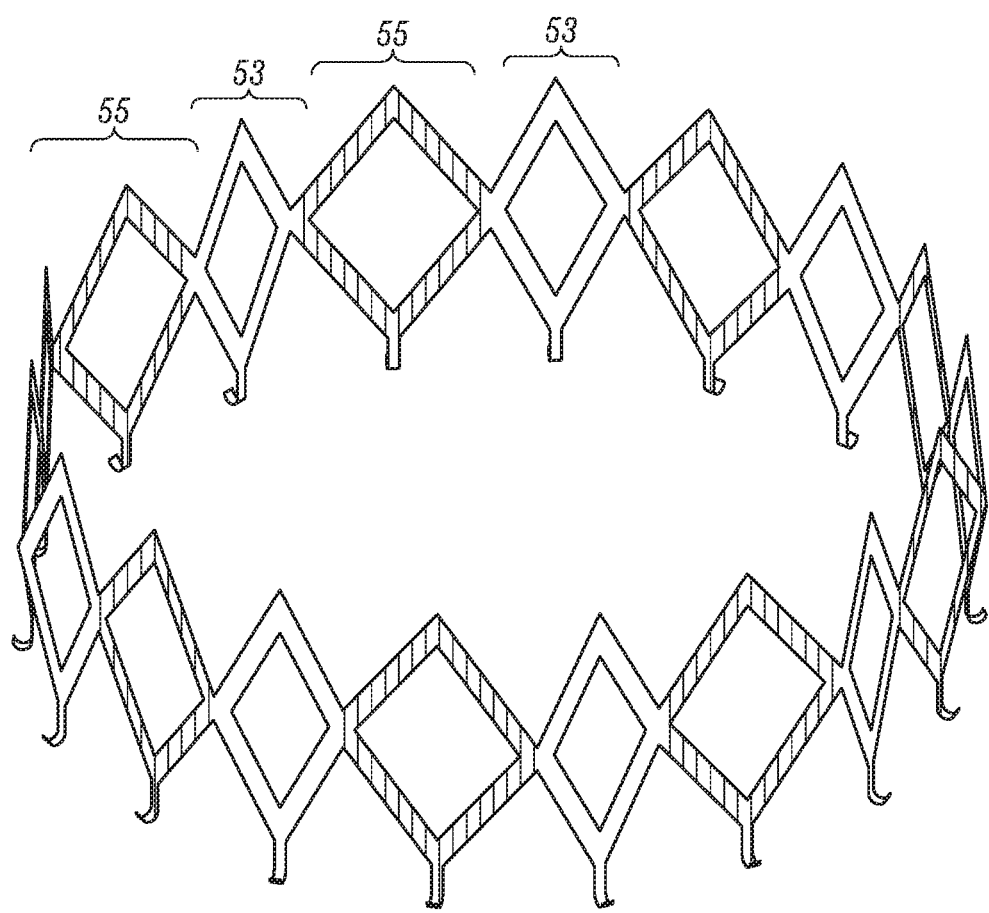
FIG. 8B depicts the device of FIG. 8A with the shape memory portions retracted back to the shape set position.

The embodiment depicted in FIGS. 8A and 8B is formed of alternating shape memory and non-shape memory materials. A first set of strut portions 53 surrounding a quadrangular space 47 may be made of, for example, Nitinol, as depicted by the unshaded strut portions in FIG. 8A. A second set of strut portions 55, depicted by the shaded strut portions in FIG. 8A, may be made of a non-shape memory material such as stainless steel. FIG. 8B shows the device of FIG. 8A in its contracted state. Only the strut portions of shape memory material would contract after expansion. The embodiment of FIGS. 8A and 8B depicts alternating sets of shape memory and non-shape memory struts. However, shape memory and non-shape memory materials may be combined in other patterns without deviating from the concept of the embodiment.

Alternative embodiments of the frame 42 may include non-uniform patterning of the struts 48, 50. For example, the struts may vary in their width, thickness and/or proximity to each other depending upon their location on frame 42. Variability in strut patterning serves to create frames with different, non-circular shapes. For example, a non-uniform strut pattern may be designed that specifically places more constrictive force on a particular region of the mitral valve annulus 8.

An example delivery system is depicted in FIG. 9. The delivery system 60 includes at least the following components; catheter 62, guide wire 66, and balloon 64. The balloon 64 may include portions with varying diameters. For example, the proximal portion 65 of the balloon 64 depicted in FIGS. 5A and 9 is narrower than the distal portion 63. Alternatively, the balloon 64 may be tapered in shape such that the proximal portion 65 is narrower than the distal portion 63. In some embodiments, the surface of the balloon may include bumps, ridges, and/or other friction-increasing elements to prevent the device 40 from slipping along the length of the balloon 64. The balloons may be formed of, for example, polyethylene terephthalate, Nylon, or a composite material. Other suitable materials may be used as well.

Figure 9A:
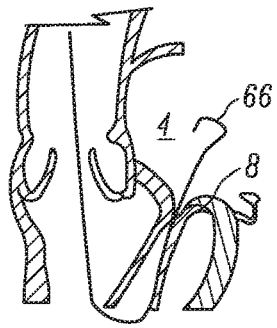
FIGS. 9A-F depict a method of delivering a mitral valve repair device using a balloon with multiple diameters.
Figure 9B:
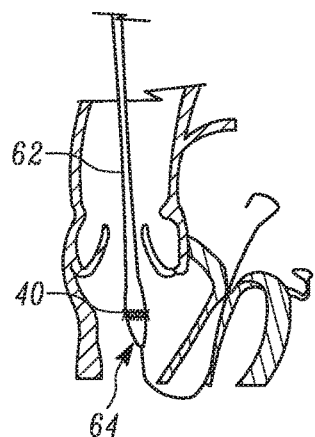
Figure 9C:
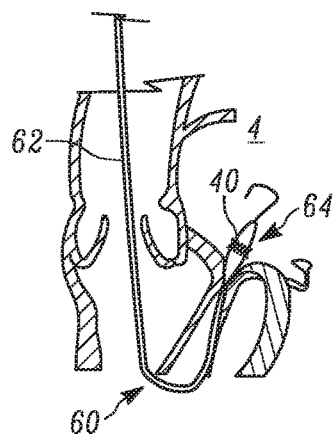

FIGS. 9A-F show an example method of delivering a mitral valve repair device. The methods of mitral valve repair disclosed herein may include a variety of approaches to reach the mitral valve including, for example: transseptal, transapical, transfemoral, transatrial, and/or transaortic approaches. The exemplary method of FIGS. 9A-F depict a transfemoral approach, wherein the device is tracked through the femoral artery and into the left ventricle. FIG. 9A shows a guide wire 66 that has been threaded through the left ventricle, through the mitral valve annulus 8, and into the left atrium 4. A delivery catheter 62 containing the mitral valve repair device 40 is run along the guide wire 66, as shown in FIG. 9B. The distal end of the catheter 62 is positioned within the left atrium 4, as shown in FIG. 9C. The catheter, in some embodiments, may employ similar bending mechanisms as those described in U.S. Pat. No. 7,780,723, which is hereby incorporated by reference in its entirety.

Figure 9D:
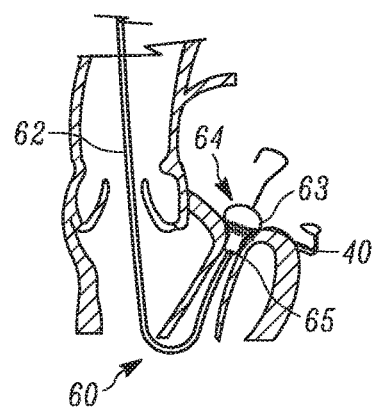
Figure 9E:
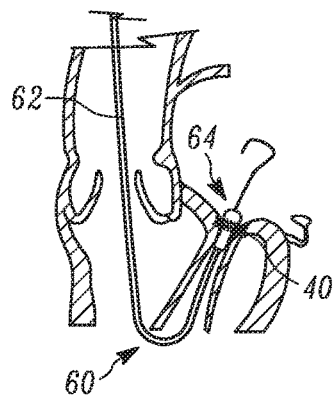
Figure 9F:
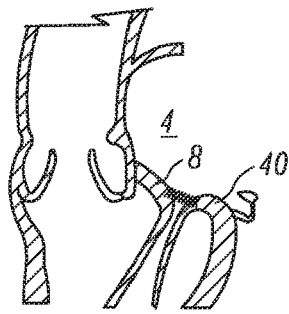

The balloon is positioned such that, upon inflation, its narrower, proximal portion 65 is between the leaflets 10, 12 of the mitral valve, as shown in FIG. 9D. The proximal portion 65 of balloon 64 serves to hold the native mitral valve in an optimal shape. The wider, distal portion 63 expands the device 40. The device 40 is positioned such that the tissue penetrating members 52 are approximately 1-5 mm from the mitral valve leaflets. After the positioning of the device 40 is verified, the surgeon induces a proximal movement of the delivery system 60. This proximal movement pulls the tissue penetrating members 52 of the device 40 into the mitral valve annulus 8 and/or the surrounding leaflet tissue. This causes the tissue penetrating members to be embedded into the tissue in a simultaneous or nearly simultaneous fashion. Once the device 40 is deemed secure, the balloon 64 may be deflated and the delivery system 60 removed from the subject, as shown in FIGS. 9E-F. Rapid pacing may be used to ensure stable deployment of the implant and good engagement of the tissue penetrating members into the tissue.

In method embodiments utilizing a shape memory frame 42 that is pre-set in an expanded state, the delivery system 60 may also include an additional delivery sleeve placed around the frame 42. Once the frame 42 is positioned above the mitral valve (in the left atrium 4), the sleeve is retracted to enable expansion of the frame into the pre-set, expanded state. A balloon 64 may be included in the delivery system 60 of this implementation, at least in order to facilitate positioning of the device 40.

Other embodiments of the balloon 64 or alternative methods of using the balloon may be employed. For example, a tapered balloon with a wider distal end 63 may help to push the tissue penetrating members into the mitral valve annulus 8 when the surgeon induces a proximal movement of the delivery system 60. Alternatively, the balloon's diameter may increase in a step-wise fashion along its axis in a distal direction. In either case, when the surgeon induces a proximal movement, the wider wall of the distal-most portion of the balloon 64 abuts the frame to push the tissue penetrating members into the annular tissue 8.

In another embodiment, the device 40 may be expanded by a perfusion balloon or other expandable structure that, upon inflation, has a lumen that enables blood to flow through the valve during the surgical procedure. This facilitates slow inflation and precise deployment of the tissue engagement members 52. A perfusion balloon may be deflated slowly, or re-inflated if the tissue engagement members 52 are not properly engaged with the tissue. In some implementations, methods incorporating perfusion balloons may be performed without rapid pacing and under normal or close to normal hemodynamic conditions. In some implementations, the perfusion balloon may also incorporate a tri-slit sleeve to function as temporary leaflets.

Figure 10:
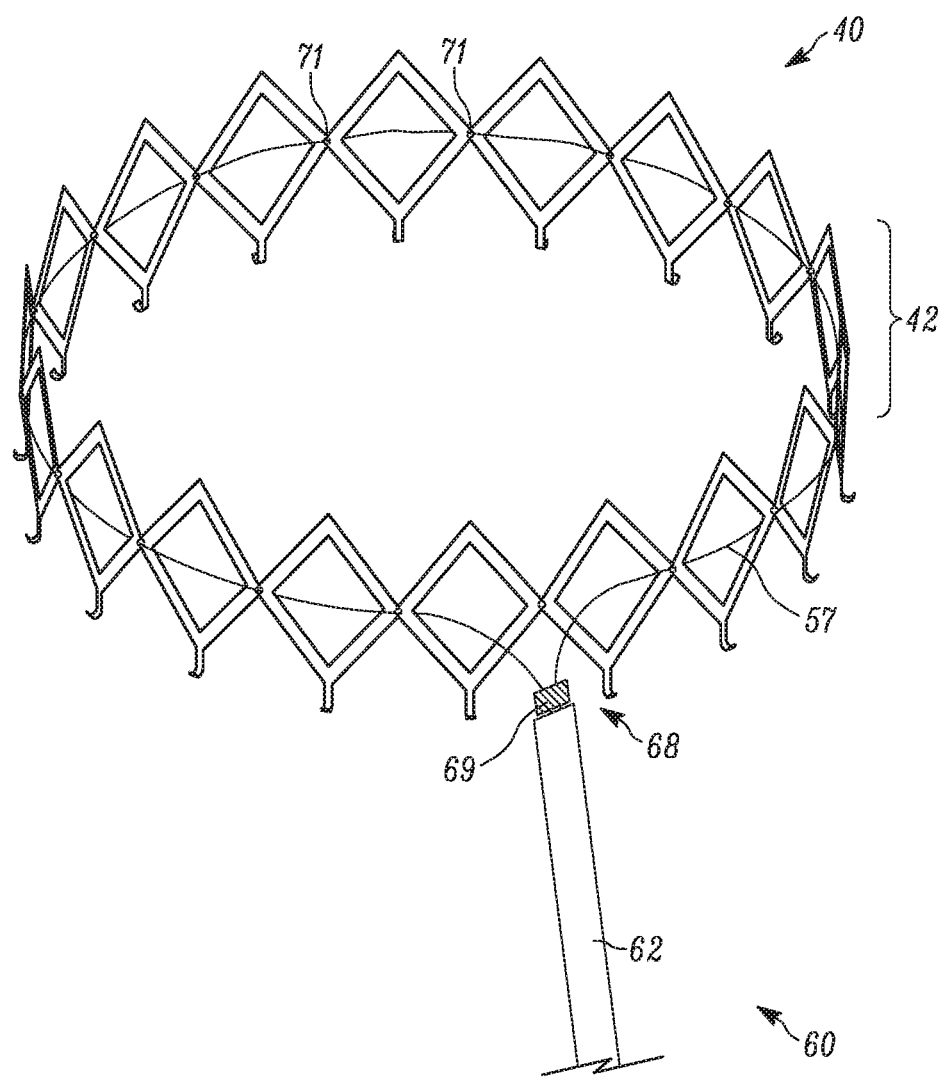
FIG. 10 depicts a device for mitral valve repair including a cinching system for adjusting the diameter of the device.

The devices 40 and/or delivery systems 60 may include additional components for adjusting the diameter of the mitral valve repair device 40. For example, as seen in FIG. 10, the device may include a diameter-adjusting suture 57. The suture 57 may be threaded through holes 71 in the frame 42. Alternatively, the suture 57 may be threaded through the voids formed between struts within the frame structure. The corresponding delivery system 60 may incorporate a cinching system 68 which is deployed from the delivery catheter 62. For the embodiment shown in FIG. 10, the cinching system 68 includes a locking mechanism 69, which secures the suture 57. The securement of the suture 57 stabilizes the diameter of frame 42.

Figure 11A:
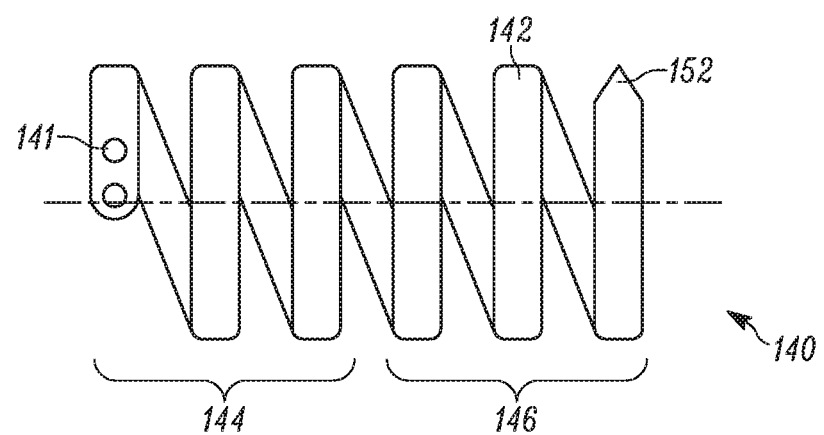
FIG. 11A depicts a device for mitral valve repair. The device includes a spiral shaped tissue penetrating member.
Figure 11B:
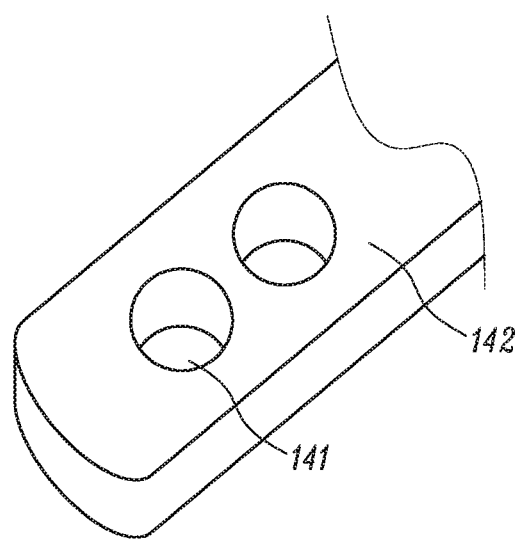
FIG. 11B is an enlarged view of a portion of the device of FIG. 11A. The enlarged view highlights the retrieval feature.

Some embodiments of mitral valve repair device may be spiral shaped, as in device 140 of FIGS. 11A and 11B. The device 140 shown in FIG. 11A includes a spiral shaped frame 142 having a distal portion 144, a proximal portion 146, and a tissue penetrating member 152 located on the proximal side of the proximal portion 146. The device 140 may also include at least one hole 141 for attaching a retrieval suture. A portion of an example device 140 having two holes 141 is shown in FIG. 11B.

Figure 12A:
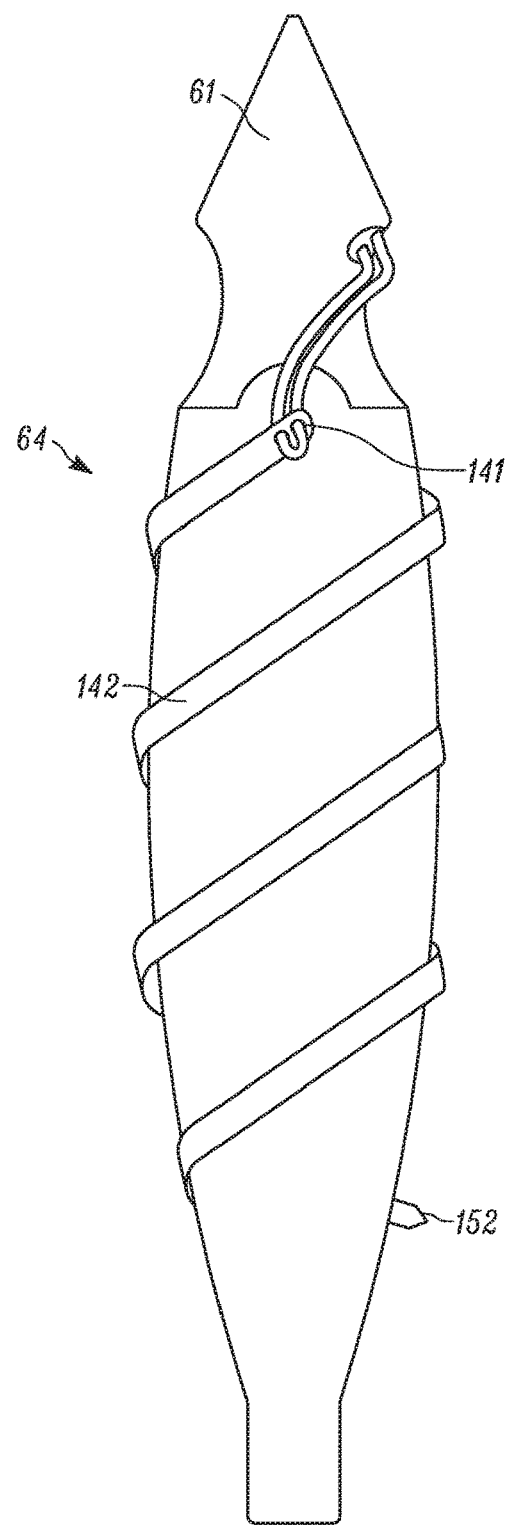
FIG. 12A depicts the collapsed device of FIG. 11A mounted onto an uninflated balloon.
Figure 12B:
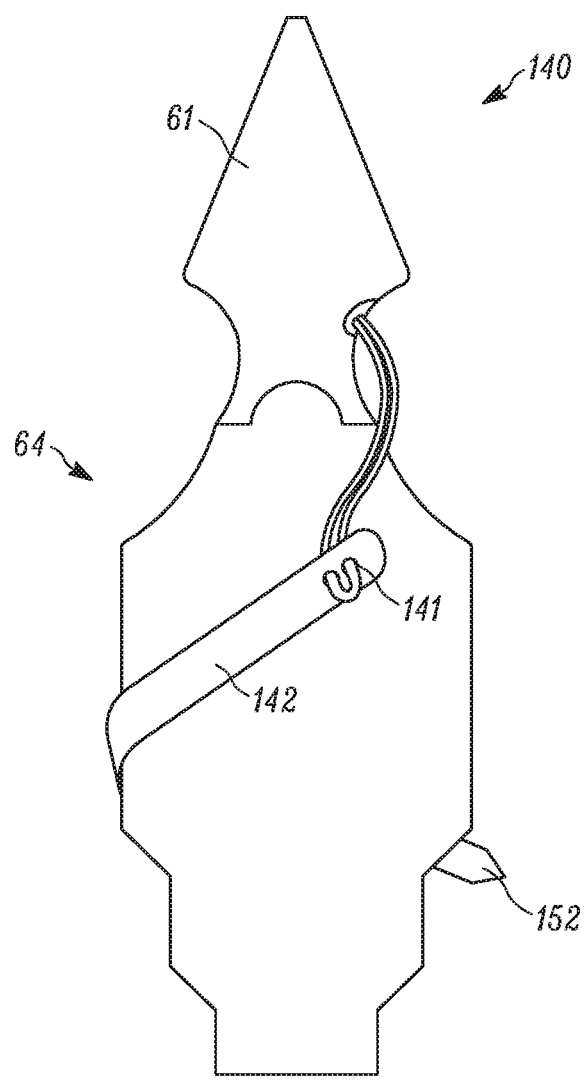
FIG. 12B depicts the expanded device of FIG. 11A mounted onto an inflated balloon.

FIG. 12A shows an example spiral-shaped device 140 in a collapsed state around delivery balloon 164. A retrieval suture 143 attaches to the retrieval holes 141. The other end of the retrieval suture 143 may be attach to nose cone 161. Upon inflation of the balloon 164, the coil of the frame 142 is partially unwound. FIG. 12B shows the device 140 in an expanded state upon an inflated balloon 164.

Figure 13A:
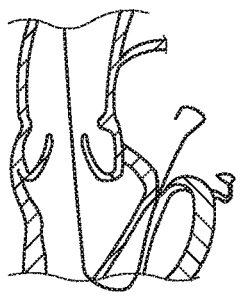
FIGS. 13A-F show a representative method of delivery for the device shown in FIG. 11A.
Figure 13B:
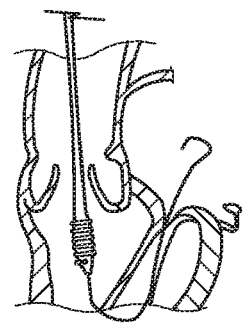
Figure 13C:
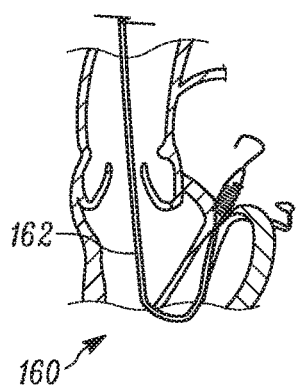
Figure 13D:
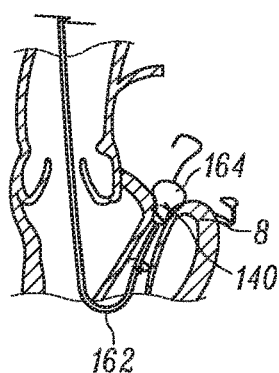
Figure 13E:
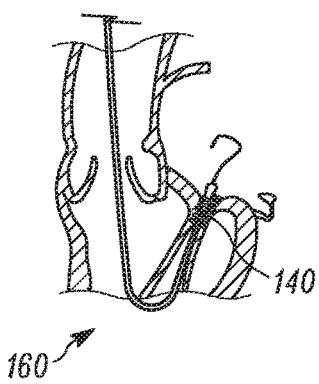
Figure 13F:
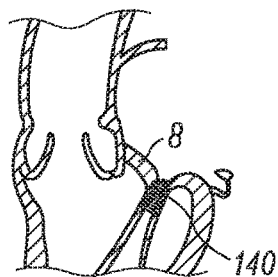

FIGS. 13A-F depict an example method for deploying the device 140 of FIGS. 12A and 12B to the subject's mitral valve. This device is routed to the mitral valve area in a manner similar to that shown in FIG. 9A-F. Once the balloon 164 is inflated between the mitral valve, as shown in FIG. 13D, the shaft of the catheter 162 is rotated. This rotation drives the tissue penetrating member 152 (shown in FIG. 12B, for example) into the mitral valve annulus 8. Continued rotation drives the device 140 around the annulus, as shown in FIG. 13E.

In some rotated implementations, a hypotube may be slid over device 140 after it has been embedded in the annulus (not shown). The hypotube may be laser-cut or heat shaped, and could serve to further reshape the annulus. In other rotated implementations, the annulus 8 is circumscribed by the hypotube before the device 140 is deployed. Once the hypotube is embedded, device 140 is tracked through the inner lumen of the larger hypotube, allowing for additional opportunities to reshape the annulus. In some implementations, multiple hypotubes may be deployed over one another. Once the annulus 8 is circumscribed by device 140 and/or the hypotube(s), the delivery system 160 is removed.

The mitral valve repair device 140 may be made of a metal or a polymer. In some embodiments, the device 140 is made of a shape memory material. For example, a shape memory mitral valve repair device 140 may be set in a collapsed state prior to deployment, then expanded by a balloon 164 during deployment. After the embedding of the device 140 and removal of the delivery system 160, the device returns to its collapsed, coiled state. This exerts an inwardly constrictive force on the annulus 8. Some embodiments may include electronic systems to facilitate remote mechanical adjustments to the shape of the device 140, similar to those described in U.S. Pat. Nos. 7,507,252 and 7,695,512, which are hereby incorporated by reference in their entireties. These remote adjustments may be assisted by echocardiography, fluoroscopy, and the like.

Figure 14A:
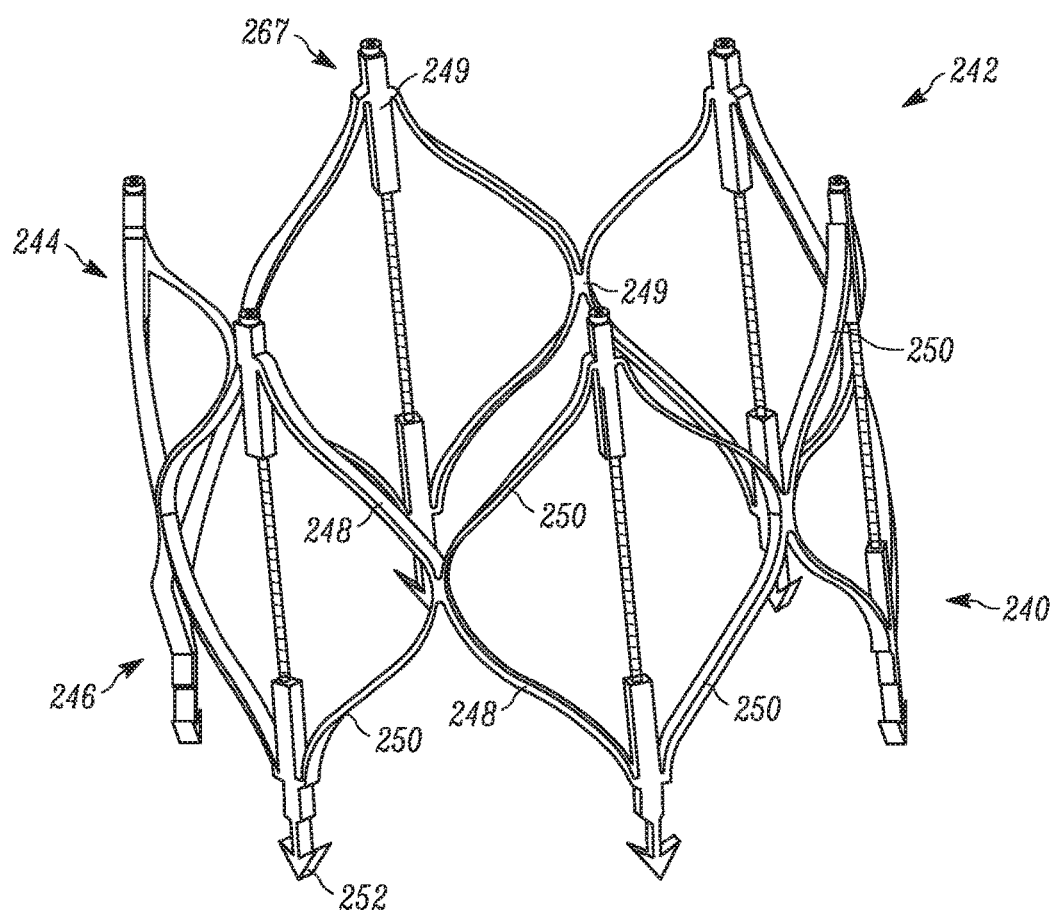
FIG. 14A shows a device for mitral valve repair in an expanded state. The device may be mechanically expanded or contracted via expansion features.
Figure 14B:
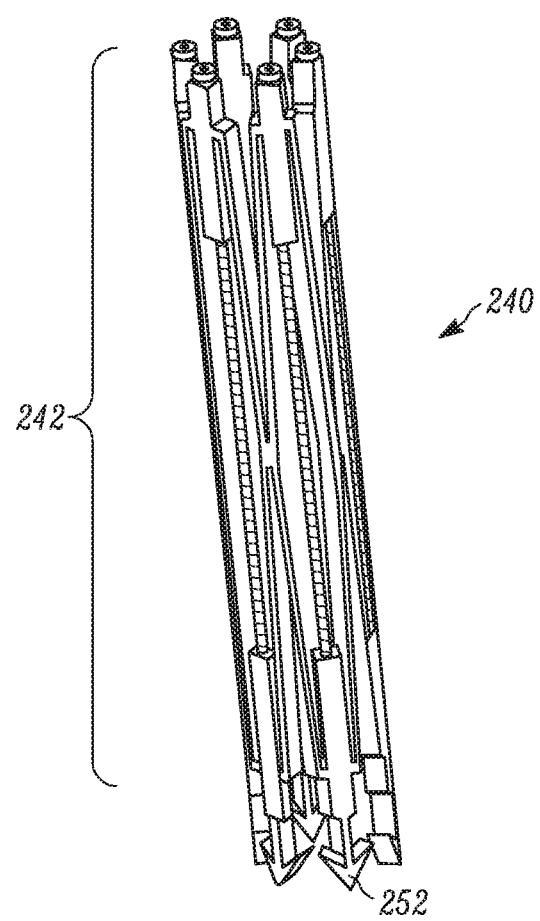
FIG. 14B shows the device of FIG. 14A in a collapsed state.

FIG. 14A shows an example embodiment of a mechanically controllable device 240 for mitral valve repair. Device 240 may be used to perform mitral valve annuloplasty, or to serve as a clocking station for a transcatheter prosthetic heart valve. Device 240 includes a frame 242 including a distal portion 244 and a proximal portion 246. The frame includes a first series of struts 248 and a second series of parallel struts 250. The first and second series of struts meet at connection points 249. Strut connection points 249 are located at the proximal and distal ends of frame 242, as well as at least one central location along the length of the frame. The device 240 may be urged into a collapsed state, as shown in FIG. 14B. This collapsed state may allow, for example, for delivery of the device 240 through a catheter to the surgical site.

Figure 15A:
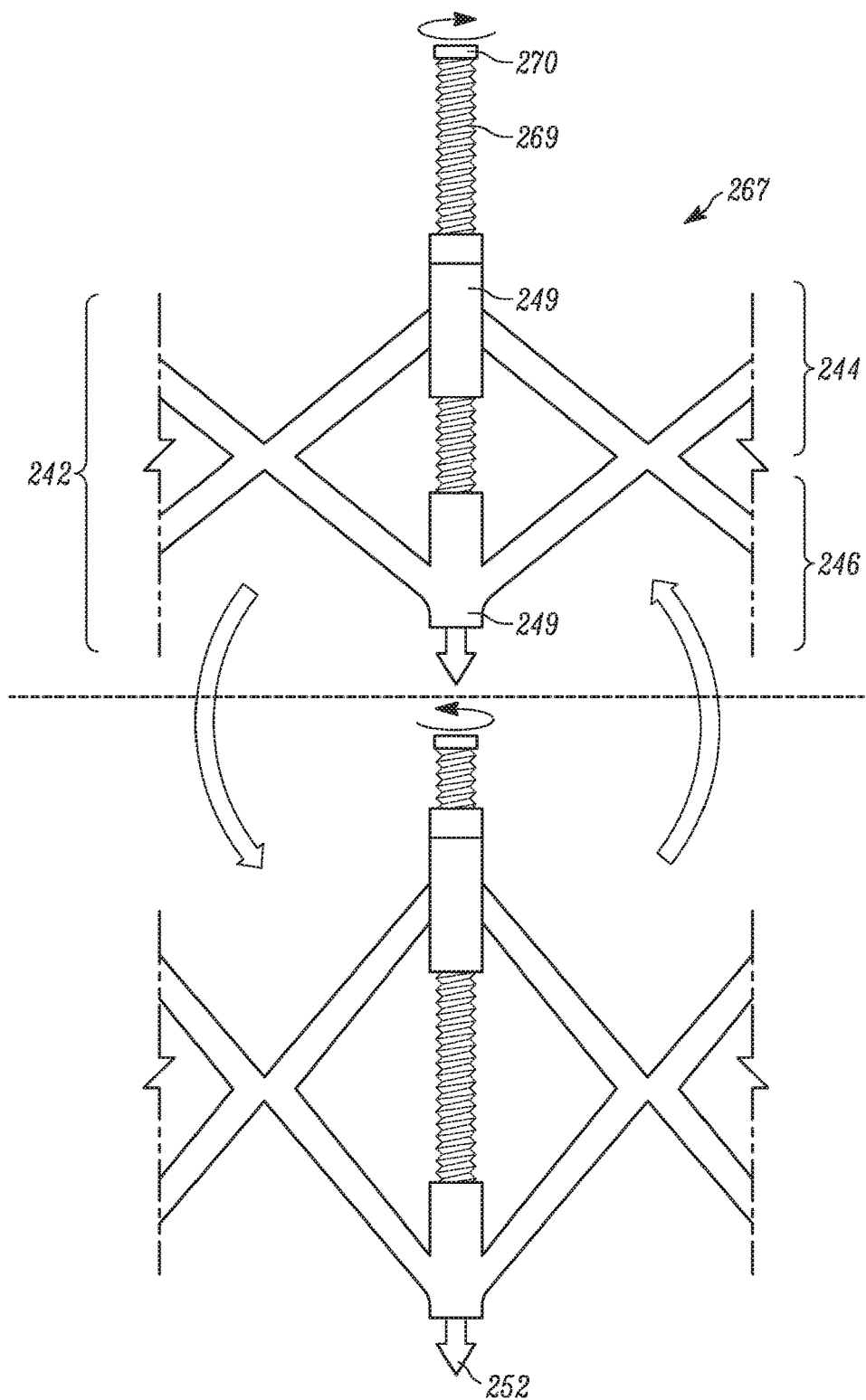
FIG. 15A is an enlarged view of an expansion feature for a mechanically controlled device for mitral valve repair depicting the mechanism of expansion.
Figure 15B:
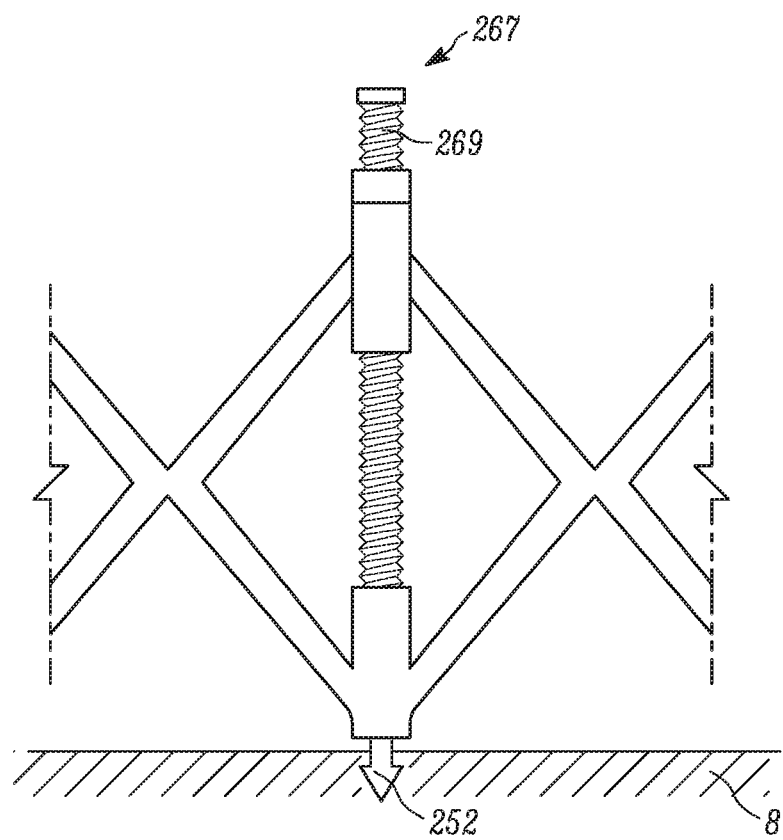
FIG. 15B depicts the expansion feature of 15A as a tissue penetrating member pierces the valvular tissue.
Figure 15C:
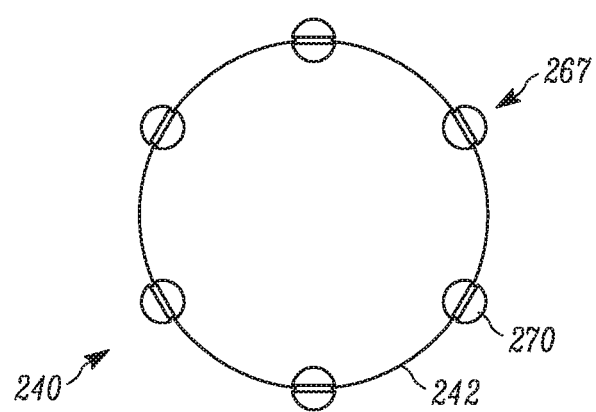
FIG. 15C is a top view of the devices depicted in FIGS. 14A-B and 15A-B.

The embodiment of FIGS. 14A and 14B has an adjustable diameter facilitated by at least one expansion feature 267. The expansion features 267 may be mechanically controlled. An exemplary expansion feature 267 is shown in detail in FIG. 15A. Expansion feature 267 has a screw head 270 and a screw shaft 269 that is threaded through a first strut connection point 249 on the distal portion 244 of the frame and into a second strut connection point 249 on the proximal portion 246 of the frame. Rotation of the screw shaft 269 results in expansion or collapse of the frame 242, depending on the direction of rotation. As shown in FIG. 15B, the rotation of the screw shaft 269 helps to drive the tissue penetrating member, 252, into the annular tissue 8. A top view of this embodiment, indicating the positioning of the expansion features 267, is shown in FIG. 15C.

The material used to make the embodiment of device 240 shown in FIGS. 14A-B and 15A-C may be a shape memory or non-shape memory material. For a shape memory material, the frame 242 may be set in a collapsed state prior to deployment. After deployment, the expansion features 267 serve to keep the frame open. For a non-shape memory material, the expansion features 267 would serve to secure the frame 242 in its final state. The presence of expansion features 267 allows for a reduction in the amount of material used for the struts 248, 250 of the frame. The profile of the fully collapsed device 240 may be between 15-25 French, for example, 20 French.

Figure 16A:
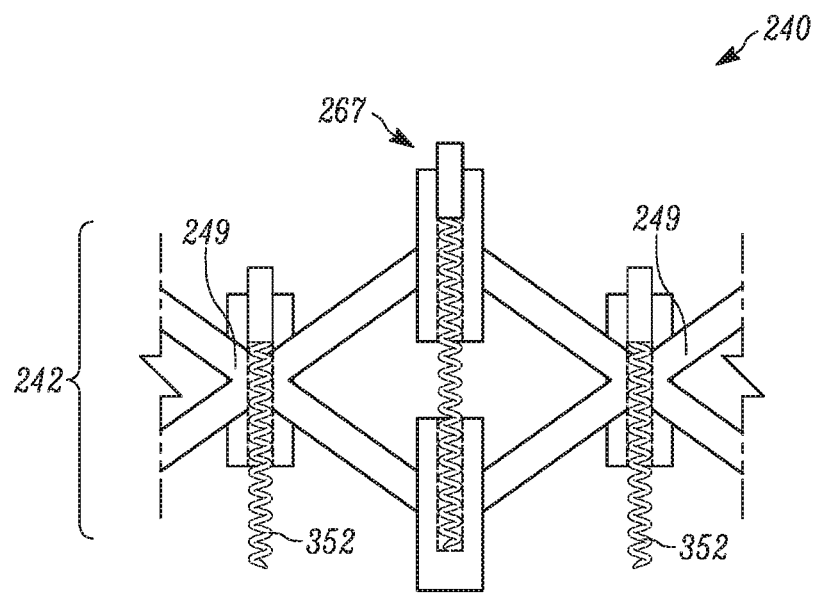
FIG. 16A is a cross section of a device for mitral valve repair. The device includes expansion features and separate tissue penetrating members.
Figure 16B:
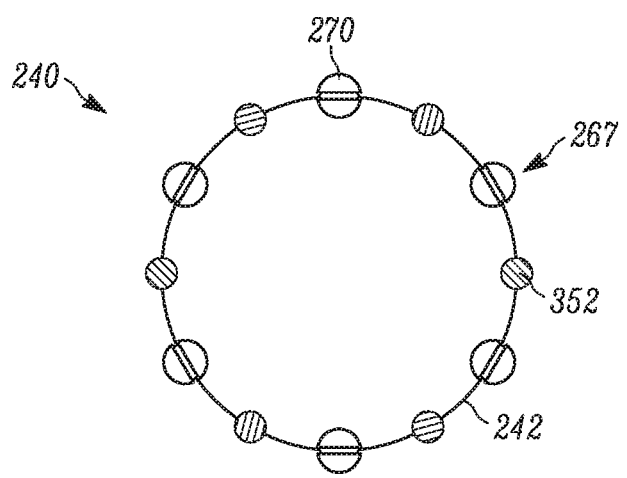
FIG. 16B is a top view of the device of FIG. 16A.

FIG. 16A shows an example embodiment of a device 240 having another tissue penetrating member 352. In this example, the tissue penetrating members 352 are helical screws that extend through strut connection points 249. FIG. 16B shows a top view of this embodiment, including the expansion feature 267 screw heads 270 as well as the tops of the helical screw tissue penetrating members 352.

Figure 17:
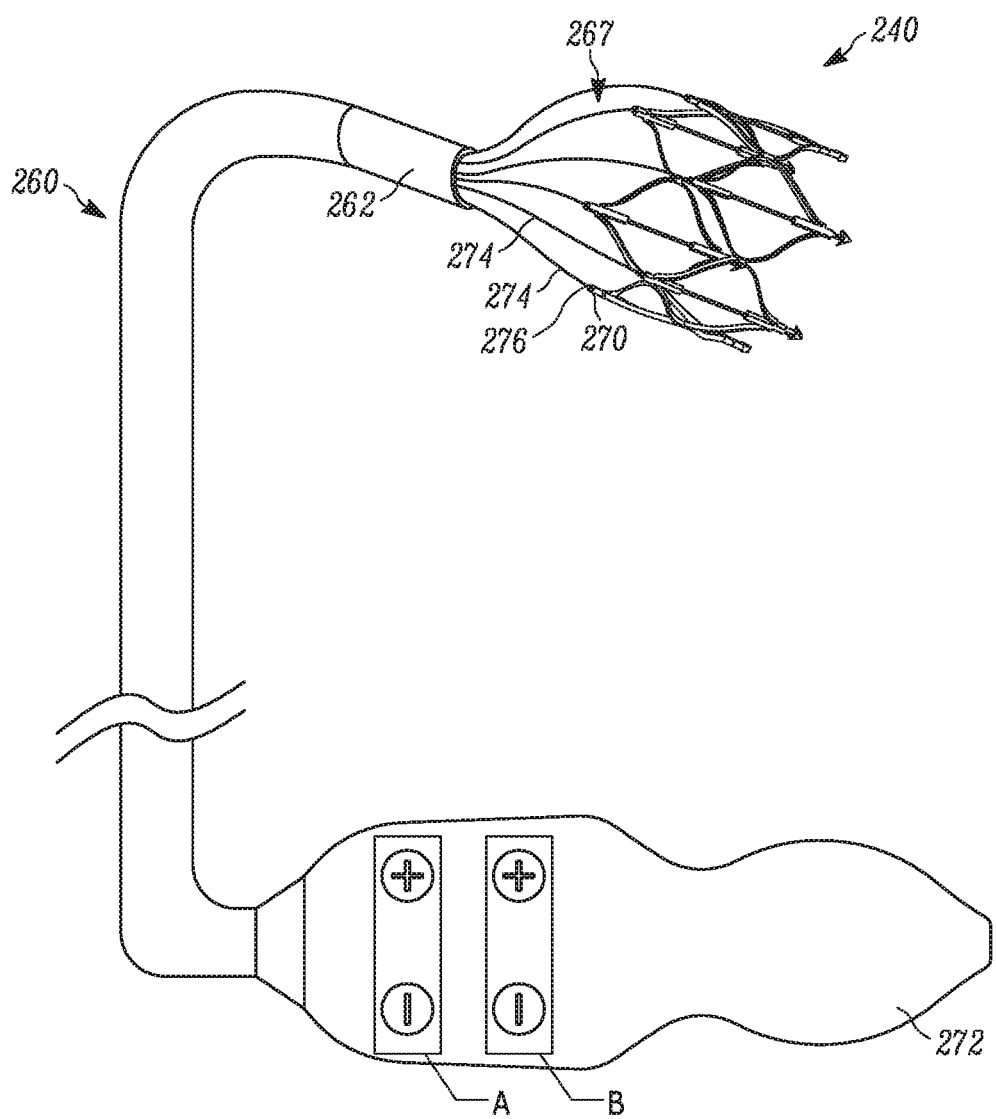
FIG. 17 depicts a delivery system for a mechanically controllable device for mitral valve repair.

FIG. 17 shows an exemplary delivery system for a device such as the embodiments of device 240 shown in FIGS. 14-16. The system includes a delivery catheter 262 as well as a handheld control device 272 for controlling the expansion features 267 of the device 240. A torque shaft mechanism may be used to manipulate the expansion features 267 and/or the tissue penetrating members 352. The torque shaft mechanism may be partially housed within the delivery system 260. The torque shaft mechanism includes rotation members 274, and at least one motor that drives the rotation of the rotation members 274. The rotation members 274 extend from the motor, through the delivery system 260 and out the distal end of the delivery system 260. The rotation members 274 may terminate in keys, for example, hex keys 276, that engage the screw heads 270 of expansion features 267. In some implementations, the rotation members 274 may engage the ends of the tissue penetrating members 352. The motor of the torque shaft mechanism therefore drives the rotation of expansion features 267 and/or tissue penetrating members 352 via the rotation members 274. In some implementations, a first motor is provided to induce rotation of the expansion features 267, and a second motor is provided to induce rotation of the tissue penetrating members 352, such that expansion and tissue engagement may be separately controlled.

The handheld device 272 shown in FIG. 17 may have separate control areas A, B for separating diameter adjustment controls from the tissue engagement controls. For example, control area A may operate a first motor of the torque shaft mechanism that drives rotation of the expansion features 267. Control area B may operate a second motor of the torque shaft mechanism that drives rotation of the tissue penetrating members 352. Therefore, control area A may be used to increase or decrease the diameter of the device 240, while control area B may be used to move the device 240 in a manner that causes the device 240 to engage the patient's tissue in a desired location.

Figure 18A:
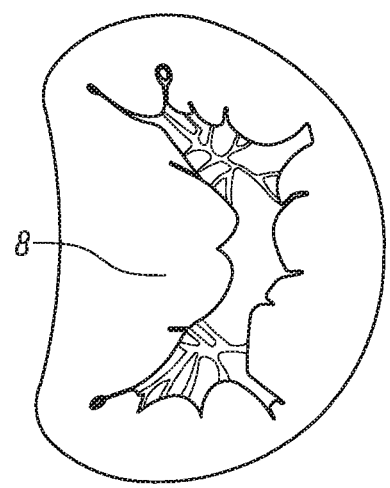
FIGS. 18A-C are views of the mitral valve from the left atrium during different stages of the valve repair procedure using the device of FIGS. 16A-B.
Figure 18B:
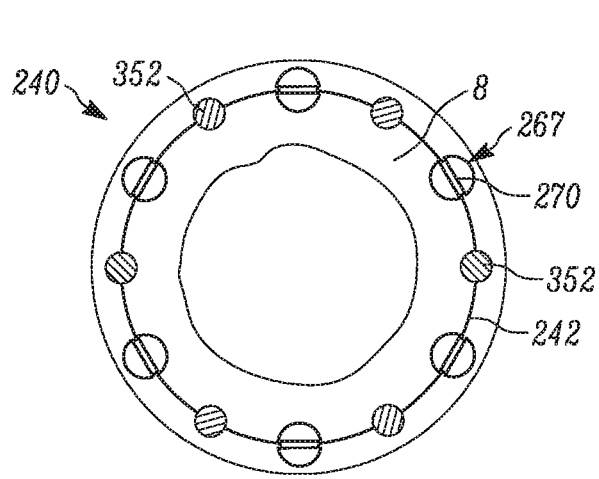
Figure 18C:
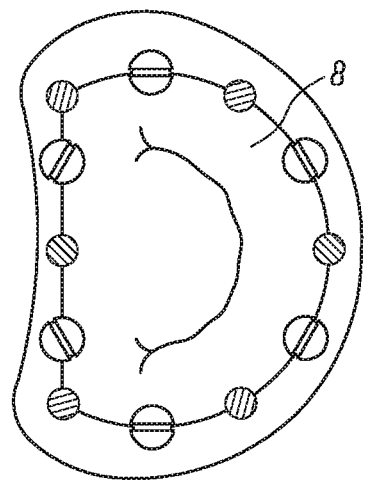

FIGS. 18A-C show an example embodiment of a device 240 being deployed on an annulus 8. FIG. 18A shows the annulus 8 prior to deployment of the device 240. As shown in FIG. 18B, the annulus 8 initially conforms to the fully expanded frame 242. During this phase the annulus 8 may initially be expanded via a balloon or other expansion means. Next, the expanded annulus 8 may be pierced by tissue penetrating members 252 and/or 352. Helical screw tissue penetrating members 352 may be mechanically controlled to ensure tissue engagement. In some implementations, the tissue penetrating members 252 and/or 352 may be embedded into the tissue in a simultaneous or nearly simultaneous fashion. Not every tissue penetrating member must penetrate the annulus 8, however. In some embodiments, for example, only certain tissue penetrating members may penetrate the annulus 8. Additionally or alternatively, the screw heads 270 of the expansion features 267 may be individually tightened to customize the shape of the ring to the patient's needs. These methods can be used to adjust the device 240 such that the mitral valve is repaired with improved precision. The implant may be checked for mitral valve leaks during the procedure by echocardiography or similar methods to confirm the functionality of the device 240. FIG. 18C shows the device 240 after adjustments have been made to the shape of the frame 242.

The mechanically controlled device 240, delivery system 260, and method of delivery have several advantages that may be useful for certain patients or conditions. For example, the expansion features 267 can be manipulated either individually or as a unit. Some of the expansion features 267 may be tightened to a greater extent than others to create customized frame shapes, such as the one seen in FIG. 18. The helical screw tissue penetrating member 352 may be reversibly engaged to the tissue, allowing for adjustments if necessary. Finally, an additional advantage of the mechanically controlled embodiments described above is that blood may continue to flow through the native valve during delivery.

Figure 19A:
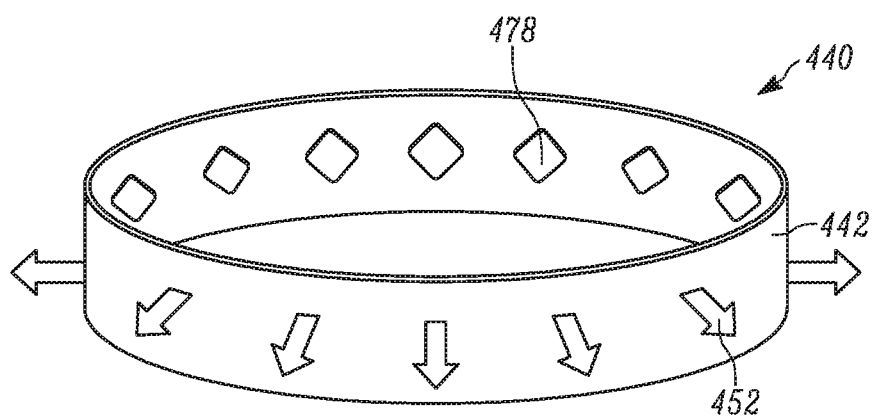
FIG. 19A depicts a device for mitral valve repair to be used in conjunction with a transvascular prosthetic heart valve.
Figure 19B:
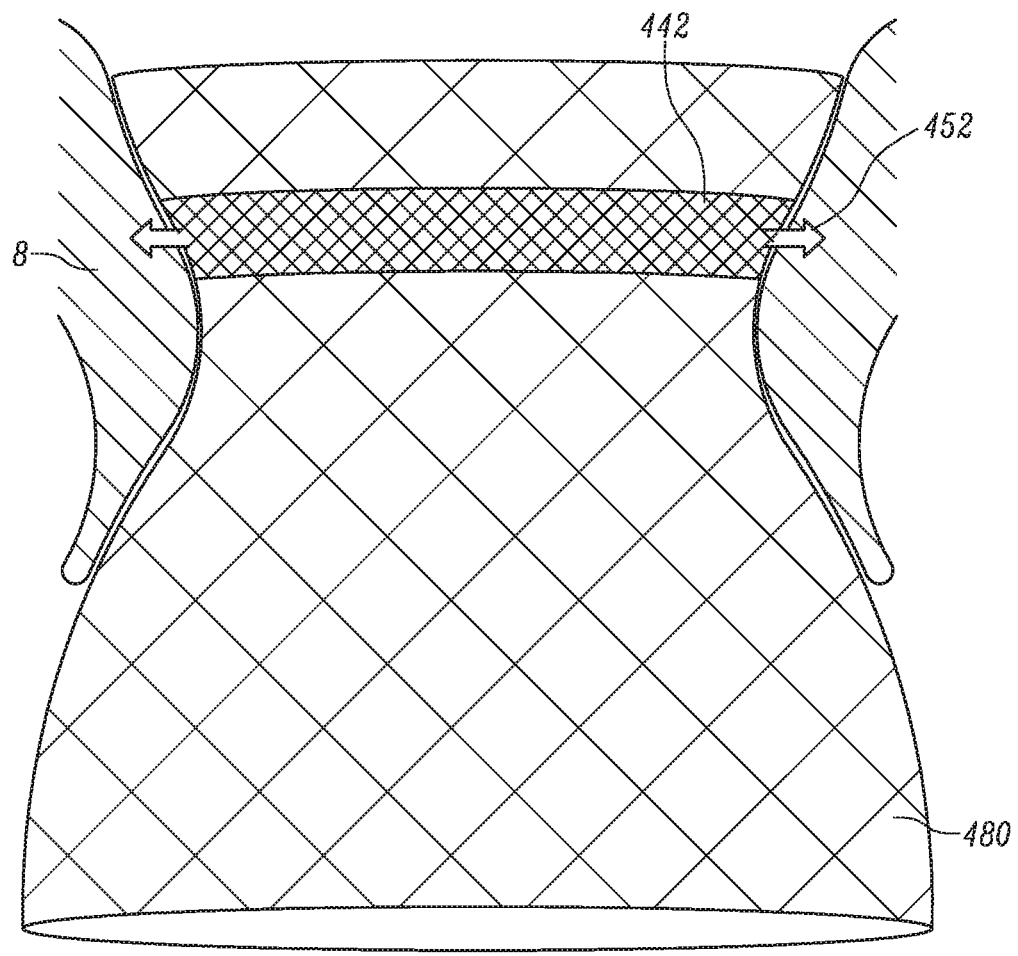
FIG. 19B is a side view of a transvascular heart valve secured to the mitral valve tissue by the device of FIG. 19A.
Figure 19C:
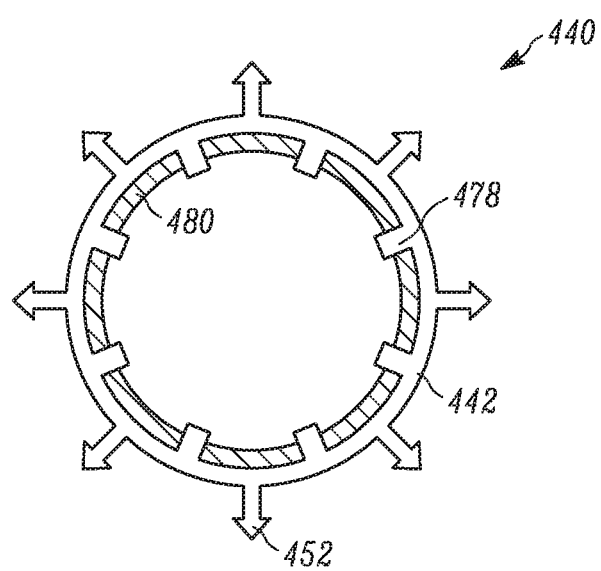
FIG. 19C is a top view of the device of FIG. 19A.

FIG. 19A shows an example embodiment of a device 440 for percutaneous mitral valve repair. This embodiment may be used, for example, as a docking station for a transcatheter heart valve (THV). As shown in FIG. 19A, the device 440 includes a frame 442 and tissue penetrating members 452 extending outwardly from the frame. FIG. 19B shows the device 440 in use as a docking station for a THV 480. The frame 442 may be solid as shown in FIG. 19A, or it may have a latticed structure as seen in FIG. 19B. The device also may also include protrusions 478 extending inwardly from the frame, as seen in FIG. 19A. The protrusions 478 may nest within spaces along the outer wall of a THV 480 to secure the THV 480 to the device 440 and thus, to the surgical location. FIG. 19C is a top view of the THV 480 nested within the frame 442 of the device 440.

For the embodiment shown in FIGS. 19A-C, the THV 480 is secured to the device 440 by nesting the diamond-shaped protrusions 478 into spaces of a latticed THV wall. However, protrusions 478 and corresponding spaces along the wall of the THV 480 may take various shapes. For example, the protrusions may be rods, bumps, ridges, or any configuration suitable for nesting within corresponding spaces located on the wall of THV 480.

Figure 20:
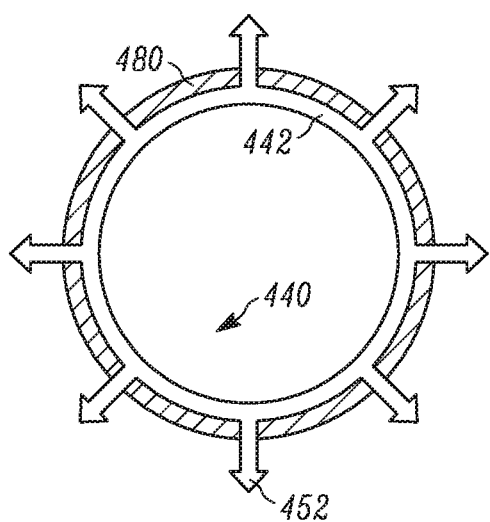
FIG. 20 is an alternate implementation of a device for mitral valve repair to be used in conjunction with a transvascular prosthetic heart valve.

Device 440 shown in FIG. 19A includes tissue engagement members 452 for securing the frame 442 to the tissue. In some embodiments, the force of expansion of the THV 480 drives the tissue engagement members 452 of the device 440 into the tissue such that the expansion of the THV 480 and the device 440 may be performed simultaneously. In other embodiments, the device 440 may be first secured to the annular tissue 8 using staples, sutures, fabric, a porous tissue fixation layer, or another securing mechanism. The THV 480 may then be expanded within the device 440 after the device 440 is secured to the tissue FIG. 20 shows an example embodiment of a device 440 that is similar to the one shown in FIGS. 19A and 19B, but lacks internal protrusions. For this embodiment, the THV 480 is deployed first to the native mitral valve. Device 440 is then opened within the lumen of the THV 480. Tissue penetrating members 452 pierce the wall of the THV 480 and secure it to the mitral valve annulus 8. The wall of THVs 480 used in conjunction with this embodiment may include of a material, such as a fabric covering, that can be punctured by the tissue penetrating members 452.

Figure 21:
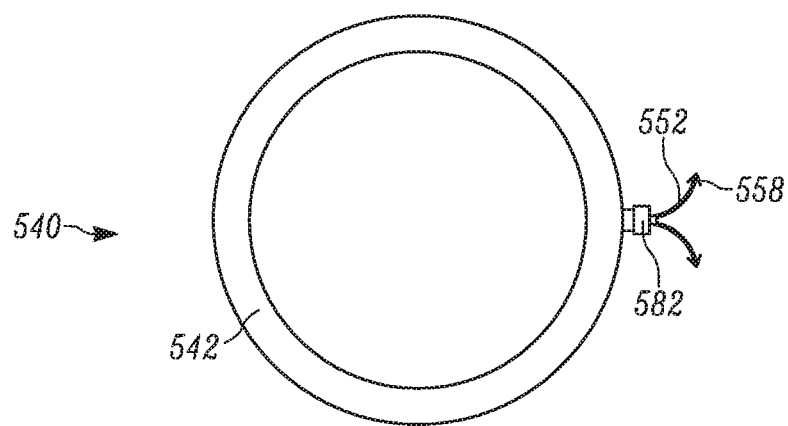
FIG. 21 is an alternate implementation of a device for mitral valve repair to be used in conjunction with a transvascular prosthetic heart valve.

FIG. 21 shows another example embodiment of a device 540 for mitral valve repair. Like the embodiments of FIGS. 19 and 20, device 540 may be used as a docking station for THV 480. Device 540 also includes a frame 542. Extending outwardly from the frame is a knob 582 for limiting movement of the device 540 during the procedure. Some implementations may include multiple knobs positioned in different locations of frame 542. Tissue penetrating members 552 protrude outwardly from the knob 582. In some embodiments, the tissue penetration members 552 may also include tissue fixation mechanisms, such as barbs 558. Barbs 558 extend away from the tissue penetrating members 552 at an angle, creating a physical barrier to slippage of the tissue penetrating members 552 within the tissue once embedded.

In one example, device 540 shown in FIG. 21 may be deployed transseptally prior to the deployment of the THV 480. The device 540 may be made of a shape memory material and expand above the mitral valve annulus 8 once released from the delivery catheter. During expansion, the tissue penetrating members 552 pierce the tissue of the mitral valve annulus 8. The device may then be further stapled or sutured to the mitral valve annulus 8 prior to delivery of the THV 480. Knob 582 and tissue penetrating members 552 limit movement of the frame 542 during subsequent stapling or suturing. Once the device 540 is secured to the annulus, it may be used to anchor the THV 480 to the native mitral valve.

For each of the embodiments in FIGS. 19-21, the devices 440, 540 and THV 480 may be delivered by a single catheter (in series), or by a separate catheter. They could be delivered from the same direction (transseptal, transapical, transfemoral, transatrial, transaortic), or from different directions. For the embodiment of FIG. 20, device 440 is deployed within the THV at a location that will not penetrate the prosthetic leaflets of the THV 480. THVs 480 used in conjunction with these embodiments may include structures for mating with the devices 440, 540. For example, THV 480 may include a flange for mating with the ring, thereby avoiding damage to the prosthetic valve structure.

THVs 480 to be used in mitral valve repair may have a shape that conforms to the mitral valve. For example, the wall of the THV may be curved and of different dimensions than THVs useful for other cardiac heart valves. Some embodiments of the methods may include devices for mitral valve repair that cooperate with THV 480 by means other than the devices disclosed above (e.g., 40, 140, 240, 340, 440, 540). For example, one or more fasteners may be used to secure the prosthetic valve directly to the mitral valve annulus 8 or to the leaflets 10, 12. The fasteners may be rivets, staples, or the like.

Although the disclosure has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments. In addition, while a particular feature of the disclosure may have been described above with respect to only one or more of several illustrated embodiments, such feature may be combined with one or more other features of the other embodiments, as may be desired and advantageous for any given or particular application.

What is claimed is:

1. A device for improving function of a cardiac valve, comprising:
   a frame configured to fit within a cardiac valve, the frame comprising an annular body having a first end, a second end, and an opening extending therebetween; and
   wherein the frame comprises a pair of tissue penetrating members extending from the first end of the frame, each tissue penetrating member comprising an end portion having a sharp penetrating surface configured to pierce valvular tissue,
   wherein the frame is collapsible to a first position and expandable to a second position;
   wherein in the first position, the pair of tissue penetrating members are positioned such that their respective penetrating surfaces abut one another to form a blunt end; and
   wherein in the second position, the pair of tissue penetrating members are spaced apart such that their respective penetrating surfaces are exposed.

2. The device of claim 1, wherein the tissue penetrating members further comprise tissue fixation mechanisms that have pointed ends positioned closer to the first end of the annular body of the frame than the penetrating surfaces of the tissue penetrating members.

3. The device of claim 1, wherein the frame is at least partially formed from a shape memory material.

4. The device of claim 1, wherein the frame comprises a plurality of intersecting struts, wherein some of the struts are made of shape memory material and some of the struts are made of non-shape memory material.

5. The device of claim 4, wherein the struts made of shape memory material and the struts made of non-shape memory material alternate along the perimeter of the frame.

6. The device of claim 1, wherein the frame is configured to retract from the second position and pull together the penetrated tissue.

7. The device of claim 1, further comprising a cinching system radially surrounding the frame and configured to adjust an overall diameter of the frame.

8. The device of claim 1, wherein the annular body of the frame comprises a plurality of intersecting struts forming a plurality of apices at the first end of the annular body, and wherein the pair of tissue penetrating members are attached to and extend axially away from one of the apices.

9. The device of claim 8, wherein the pair of tissue penetrating members are configured to pivot at the apex to which the tissue penetrating members are attached.

10. The device of claim 9, wherein each of the tissue penetrating members is an extension of one of two struts that intersect to form the apex to which the tissue penetrating members are attached.

11. The device of claim 10, wherein when the frame is expanded, the tissue penetrating surfaces pivot away from each other around a pivot axis at the apex to which the tissue penetrating members are attached.

12. The device of claim 8, wherein the frame comprises a plurality of pairs of tissue penetrating members, wherein each pair is attached to and extends axially away from a respective apex at the first end of the annular body.

13. The device of claim 1, wherein the end portion of each tissue penetrating member comprises a curved outer surface, and wherein when the frame is in the first position and the tissue penetrating surfaces are abutting one another, the curved outer surfaces form a continuous curved surface that defines the blunt end and when the frame is expanded to the second position, the curved outer surfaces are spaced from each other.

14. The device of claim 1, wherein the pair of tissue penetrating members are made of a shape memory material.

15. A method of percutaneous cardiac valve repair, the method comprising:
- providing a transcatheter delivery system comprising:
  - a catheter;
  - an elongate balloon mounted along a distal end portion of the catheter, wherein the elongate balloon comprises an inflated state and an uninflated state, and wherein the elongate balloon comprises, in the inflated state, a first portion with a first diameter and a second portion with a second diameter larger than the first diameter; and
  - a frame surrounding at least a portion of the elongate balloon and comprising an annular body having a first end and a second end;
  - wherein when the elongate balloon is in the uninflated state, the frame is in a corresponding collapsed state, and when the elongate balloon is in the inflated state, the frame is expanded to an expanded state;
  - wherein the frame comprises a pair of tissue penetrating members extending from the first end of the annular body of the frame, each tissue penetrating member comprising a sharp penetrating surface configured to pierce valvular tissue;
  - wherein when the frame is in the collapsed state, the pair of tissue penetrating members are positioned relative to each other such that their penetrating surfaces abut one another to form a blunt end;
  - wherein when the frame is in the expanded state, the pair of tissue penetrating members are spaced apart such that their penetrating surfaces are exposed;
- navigating the elongate balloon in the uninflated state and the frame in the collapsed state through the cardiovascular system of a subject via the catheter;
- positioning the elongate balloon and the frame within a cardiac valve of the subject;
- moving a gas or liquid through the catheter and into the elongate balloon, wherein said moving causes the elongate balloon to expand to the inflated state and the frame to expand to the expanded state, which causes the penetrating surfaces of the tissue penetrating members to move apart from each other;
- applying force to the catheter in a manner that causes the penetrating surfaces of the tissue penetrating member of the frame to penetrate the valvular tissue of the subject;
- deflating the elongate balloon such that the frame remains attached to the valvular tissue; and
- removing the catheter and elongate balloon from the subject.

16. The method of claim 15, wherein the frame comprises a shape memory material that causes the frame to retract from the expanded state after removal of the elongate balloon.

17. The method of claim 15, wherein positioning the elongate balloon comprises positioning the elongate balloon such that the first portion is positioned between leaflets of the cardiac valve.

18. The method of claim 15, wherein the frame surrounds at least a portion of the second portion of the balloon.

19. The method of claim 15, wherein a surface of the elongate balloon comprises a plurality of friction elements configured to increase friction between the elongate balloon and the frame.

20. The method of claim 15, wherein the frame comprises a shape memory material that is shape set in the expanded state such that the frame remains at the expanded state and does not contract after removal of the elongate balloon.

21. The method of claim 20, wherein the transcatheter delivery system further comprising a sleeve place around the frame such that retraction of the sleeve enables the frame to expand into the expanded state.

22. The method of claim 15, wherein the annular body of the frame comprises a plurality of intersecting struts forming a plurality of apices at the first end of the annular body, and wherein the pair of tissue penetrating members are attached to and extend axially away from one of the apices.

23. The device of claim 22, wherein the pair of tissue penetrating members are configured to pivot away from each other around a pivot axis at the apex to which the tissue penetrating members are attached when the frame is expanded to the expanded state.

24. The device of claim 22, wherein the pair of tissue penetrating members comprises a plurality of pairs of tissue penetrating members, wherein each pair is attached to and extends axially away from a respective apex at the first end of the annular body.

* * * * *